United States Patent
Zitvogel et al.

(10) Patent No.: US 6,849,452 B1
(45) Date of Patent: Feb. 1, 2005

(54) METHODS FOR ACTIVATING NATURAL KILLER (NK) CELLS AND MEANS FOR CARRYING OUT SAID METHODS

(75) Inventors: Laurence Zitvogel, Paris (FR); Nadine Fernandez, Paris (FR)

(73) Assignee: Institut Gustave Roussy, Villejuif Cedex (FR)

( * ) Notice: Subject to any disclaimer, the term of this patent is extended or adjusted under 35 U.S.C. 154(b) by 0 days.

(21) Appl. No.: 09/260,512

(22) Filed: Mar. 2, 1999

(30) Foreign Application Priority Data

Mar. 3, 1998 (FR) ............................................. 98 02558
Aug. 21, 1998 (FR) ............................................. 98 10636

(51) Int. Cl.⁷ ............................. C12N 5/06; C12N 5/00; A61K 48/00
(52) U.S. Cl. ....................... 435/347; 435/325; 435/372; 435/373; 435/377; 435/6; 435/7.24; 424/93.1; 424/93.3; 424/93.7; 424/192.1
(58) Field of Search ................................ 435/325, 347, 435/372, 373, 377; 424/93.3

(56) References Cited

U.S. PATENT DOCUMENTS 5,569,585 A * 10/1996 Goodwin et al. ............... 435/6
5,976,546 A * 11/1999 Laus et al. ................. 424/192.1
6,017,527 A * 1/2000 Maraskovsky et al. .. 424/93.71

FOREIGN PATENT DOCUMENTS

| WO | WO 94/02156 | 2/1994 |
|---|---|---|
| WO | WO 95/34638 | 12/1995 |
| WO | WO 97/12633 | 4/1997 |

OTHER PUBLICATIONS

Rabinowich et al. (1992) J. Immunol., vol. 149, 340–349.*
Hsu et al. (1996) Nat. Med., vol. 2(1), 52–58.*
Shah et al., Dendritic cells that have interacted with antigen are targets for natural killer cells, 1985, J. Exp. Med., vol. 162, pp. 625–636.
Leibson, Signal Transduction during Natural Killer Cell Activation: Inside the Mind of a Killer, Jun. 1997, vol. 6 pp. 655–661.*
Gorak et al., "Dendritic cells, but not macrophages, produce IL–12 immediately following *Leishmania donovani* nfection," Eur. J. Immunol. 28: 687–695 (1998).

* cited by examiner

Primary Examiner—Anne M. Wehbe
(74) Attorney, Agent, or Firm—Preston Gates Ellis & Rouvelas Meeds

(57) ABSTRACT

The present invention relates to a process for activating natural killer cells comprising bringing NK cells into contact with dendritic cells in vitro, ex vivo or in vivo. The invention also relates to cell compositions comprising activated NK cells, NK cell-dendritic cell co-cultures or dendritic cells, and to their use to stimulate the cytolytic activity of NK cells or natural immunity in vivo. The invention also relates to a NK cell stimulation factor present in the dendritic cell membrane, and to triggering media and factor(s) for dendritic cells and to their use, either alone or in combination, to stimulate NK activity, in particular in vivo. The invention can be used to control NK cell activity in vitro, ex vivo or in vivo, in particular under pathological conditions.

15 Claims, 20 Drawing Sheets

Figure 1:
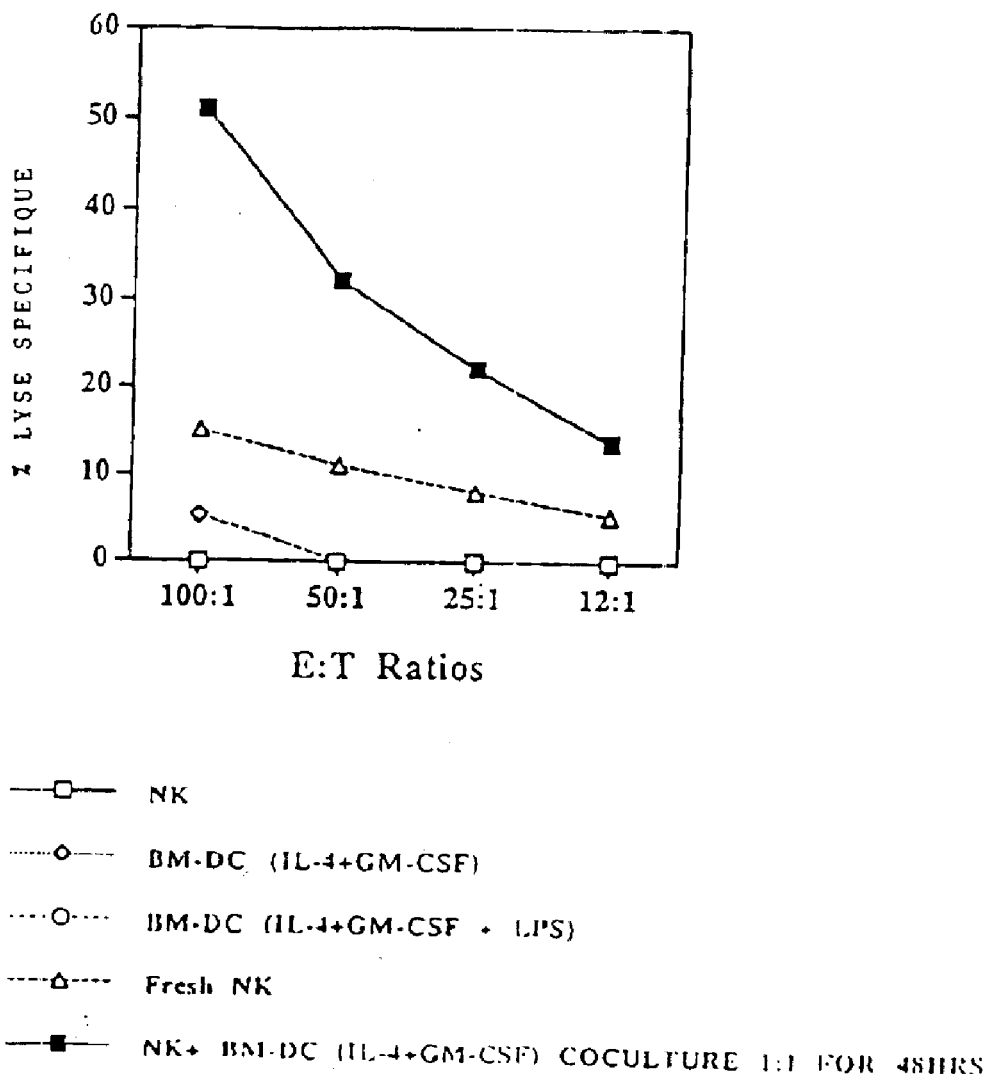

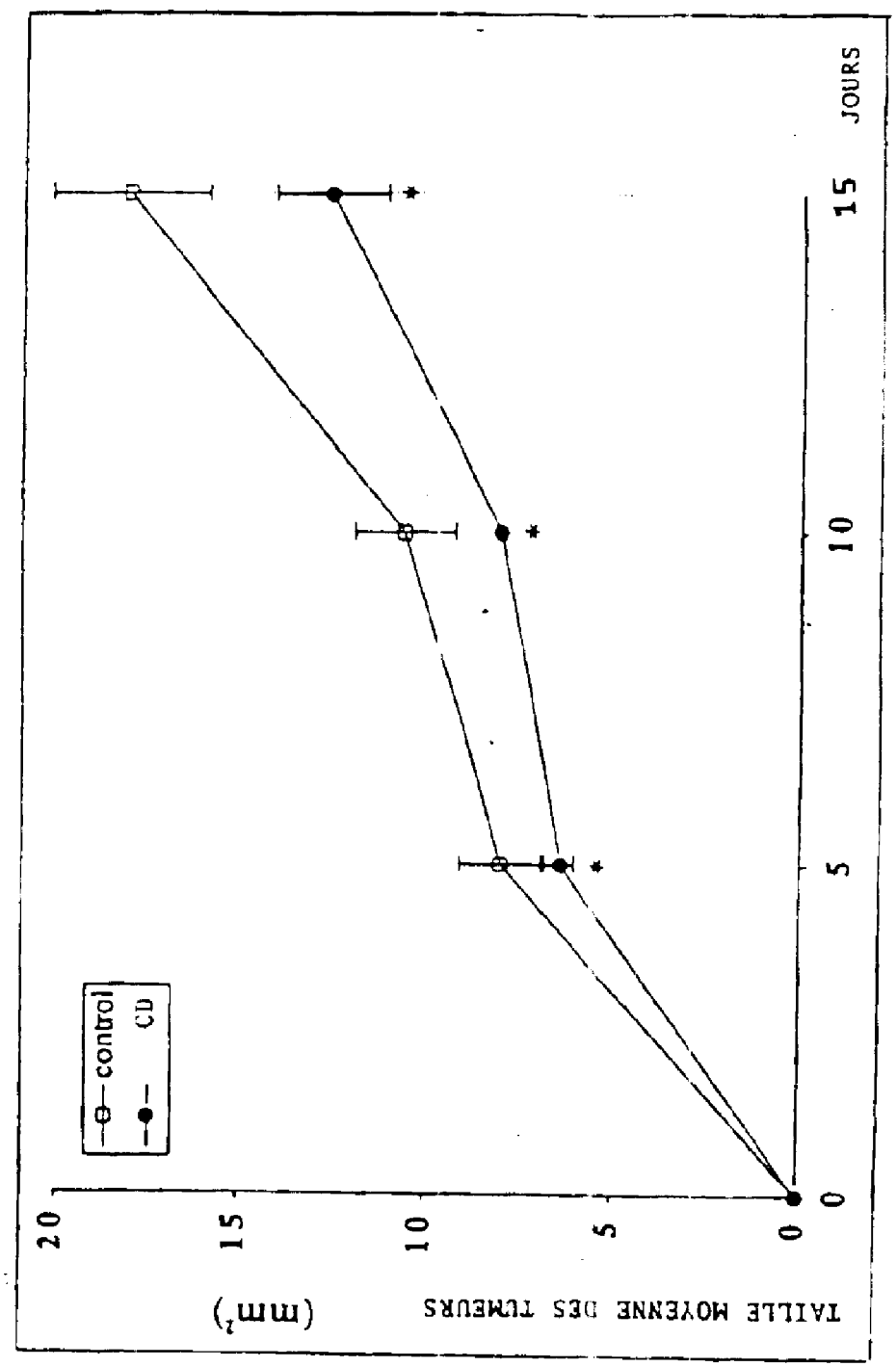
FIGURE 8.a

METHODS FOR ACTIVATING NATURAL KILLER (NK) CELLS AND MEANS FOR CARRYING OUT SAID METHODS

The present invention relates to the fields of biology and immunology. More particularly, it relates to novel methods for preparing activated natural killer cells and to means for carrying out these novel methods, in particular to novel populations of dendritic cells and products derived therefrom. It also relates to the use of the activated cells obtained using the methods of the invention in the fields of immunology, immunotherapy or, more generally, medical biotechnology.

Natural killer cells (NK cells) are a population of lymphocytes which represent a very early line of defence against viruses and tumour cells. NK cells can be characterized by the presence of CD56 and CD16 markers and by the absence of the CD3 marker. NK cells are involved in non specific anti-tumoral immunity of antigens, to prevent the establishment of primitive or metastatic tumours in the immunocompetent or immunosuppressed host. In particular, the role of NK cells in anti-tumoral immunosurveillance (primitive tumour or metastases) has been suggested in mice with tumours and treated with IL-2 and/or IL-12/IL-15, with or without LAK cells (lymphokine-activated killer cells), adherent NK cells (A-NK) or non-adherent NK cells (NA-NK) obtained ex vivo by stimulating NK cells with high doses of IL-2. In particular, NK cells appear to play a key role against tumour cells or negative class I MHC cell variants.

Because of their non-specific cytotoxic properties for antigen and their efficacy, NK cells constitute a particularly important population of effector cells in the development of immunoadoptive approaches for the treatment of cancer or infectious diseases. In this respect, anti-tumoral adoptive immunotherapy approaches have been described in the prior art. Thus in certain indications such as for patients with intensified malign lymphomas, the results of administering A-NK with small doses of IL-2 have been promising in an adjuvant situation. NK cells have also been used for experimental treatment of different types of tumours and certain clinical studies have been initiated (Kuppen et al., Int. J. Cancer, 56 (1994) 574; Lister et al., Clin. Cancer Res. 1 (1995) 607; Rosenberg et al., N. Engl. J. Med., 316 (1987) 889).

Further, such cells can also be used in vitro for non specific lysis of cells which do not express class I MHC molecules, and more generally any cell which is sensitive to NK cells.

However, adoptive therapy using NK cells (to treat murine or human tumours or other disorders such as infectious diseases) or any other in vitro or in vivo use of such cells involves ex vivo expansion and activation of the NK cells. In this respect, current techniques for activating NK cells are all based on using cytokines, generally in high doses which are not tolerated well by the host. The available data appears to indicate that NK cells do not survive ex vivo and cannot be activated without a nutritive support or without cytokines.

Thus current methods for activating NK cells in vitro involve culturing such cells in the presence of different cytokines (such as IL-1, IL-2, IL-12, IL-15, IFNα, IFNγ, IL-6, IL-4, IL-18 in certain circumstances), used alone or in combination, which activation can be considerably increased by adhesion factors or co-stimulation factors such as ICAM, LFA or CD70. Similarly, in vivo, the efficacy of NK cells in anti-tumoral immunity is not dissociable from co-administration of cytokines such as IL-2/IL-15 or IL-12, IL-18, and IL-10. IFN8 also act as activators in association with IL-2. The activation methodologies described in the prior art thus all depend on using cytokines. Such methods have certain disadvantages, however, linked to the cost of preparing the cytokines, to the toxic nature of many cytokines, which cannot be used in in vivo applications, or to the non-specific nature of many cytokines, the in vivo use of which risks being accompanied by undesirable effects. Further, since the natural killing function is often altered in patients with tumours, the possibility of collecting such cells to activate them ex vivo can be considerably reduced.

There is thus a real need for novel methods for activating NK cells. The present application provides a solution to this problem by providing novel original approaches to activating NK cells. In particular, the present application demonstrates for the first time the possibility of activating resting NK cells with another cell population. The present application also describes, for the first time, a method of activating NK cells which is not dependent on the presence of cytokines, and which can thus overcome the disadvantages described in the prior art. The present invention thus describes novel methods for preparing activated natural killer cells and means for carrying out these novel methods.

In a first aspect, the invention thus provides a method of activating NK cells comprising bringing NK cells into contact with dendritic cells. As indicated below, contact can be made in vitro, ex vivo or in vivo. It can comprise either co-culture of NK cells and dendritic cells in vitro, or incubation of NK cells in vitro or in vivo with a preparation derived from dendritic cells, in particular membranous vesicles (exosomes), or a NK cell stimulation factor originating from dendritic cells, or in vivo passive transfer of dendritic cells, or in vivo administration of one or more dendritic cell growth factors.

In a further aspect, the invention concerns the use of dendritic cells or of a preparation derived from dendritic cells to activate natural killer cells in vitro, ex vivo or in vivo.

In a further aspect, the invention concerns the use of dendritic cells or of a preparation derived from dendritic cells to prepare a composition intended to activate natural killer cells in vivo.

In a still further aspect, the invention concerns a co-culture of dendritic cells and NK cells.

In addition, the invention concerns a composition comprising an NK cell stimulation factor originating from dendritic cells.

In a yet still further aspect, the invention concerns a method for triggering dendritic cells to improve (or cause) their capacity to stimulate NK cells, also a dendritic cell triggering factor and any composition comprising it. The invention also concerns a novel population of dendritic cells, termed "triggered dendritic cells", and any composition containing them, and uses thereof.

In other aspects, the invention provides a sub-population of NK cells activated by the method of the invention and using these cells or NK/CD cell co-cultures to stimulate cytotoxic activity in vivo or in vitro against target cells sensitive to NK cells. In a further aspect, the invention also relates to methods for greatly increasing the cytolytic and IFNγ secreting activity of resting NK cells.

The invention also concerns novel therapeutic approaches, in particular for treating infectious, tumoral, autoimmune or congenital disorders or for disorders connected to transplantation, for example. In particular, the methods of the invention involve passive transfer (i) of NK cells activated by dendritic cells ex vivo, or (ii) of dendritic cells (in particular triggered dendritic cells) or a preparation derived from dendritic cells, to directly activate the NK cells in situ, or (iii) of two cell populations co-incubated ex vivo, or the method involves (iv) administration of the dendritic cell triggering factor to trigger dendritic cells in vivo such that they become capable of efficiently activating NK cells, the factor being administered alone or in association with chemokines or cytokines or dendritic cell growth factors, for example, or administration of a NK cell stimulation factor or a dendritic cell growth factor, used alone or in combination.

As indicated above, a first aspect of the invention thus concerns a method for activating NK cells using dendritic cells. This method comprises bringing NK cells into the presence of dendritic cells or a preparation derived from dendritic cells. The present invention is based on a demonstration by the Applicant of the capacity of dendritic cells to activate resting NK cells.

The results presented in the present application demonstrate that resting NK cells, co-cultivated in the presence of dendritic cells, survive and are very strongly activated for their lytic capacity and for the production of IFNγ. Further, the activated cells obtained lyse NK-sensitive targets but do not lyse LAK-sensitive targets, which differentiates this activation phenomenon from the conventional LAK phenomenon, which is IL-2 dependent. The present application also demonstrates that allogenic and autologous dendritic cells are capable of activating NK cells in vitro, and that the mechanisms of activating NK cells in the presence of dendritic cells or a preparation derived from dendritic cells does not involve IL-12, nor IL-2, nor IL-15 nor IFNα. Further, the results presented also demonstrate the involvement of an interaction between NK cells and the membranes of dendritic cells in the activation method, demonstrating the existence of a membrane factor for dendritic cells intervening in this activation. The results obtained also show that membranous vesicles produced by the dendritic cells are also capable of activating NK cells, which indicates that the NK cell stimulation factor expressed by dendritic cells is present in said vesicles.

The pertinence of this activation of NK cells by dendritic cells has also been demonstrated in vivo, in a negative class I MHC tumour model. In mice with this tumour, a single expansion of dendritic cells can eliminate the tumour in NK-dependent manner. Further, passive adoptive transfer of dendritic cells to an immunosuppressed animal deficient in T and B cells, with a tumour, also significantly slows tumour growth.

These results thus demonstrate that dendritic cells or preparations derived from dendritic cells have the capacity to induce activation of NK cells in vitro, ex vivo or in vivo, that this activation can stimulate in vitro lysis of NK sensitive cells and in vivo natural immunity of a host organism, and can thus lead to in vivo elimination of tumours, infected cells, or can be involved in other pathological processes (autoimmune diseases, graft rejection, graft versus host disease, etc. . . . ).

The results obtained in the present invention are all the more surprising since, until now, few or no studies have suggested that NK cells could be activatable in vitro by another cell type except for transfectants coding for IL-2 and/or IL-12, IL-15 and CD70. In contrast, certain studies appeared to suggest an inhibitory role for macrophages on IL-2 dependent activation of NK cells via the intermediary of PGE2.

To our knowledge, the present invention constitutes the first evidence for NK cell activation which is not dependent on cytokines and uses another cell population or a preparation or a factor derived therefrom.

More particularly, the term "activation" of NK cells within the context of the invention designates an increase in the production of IFNγ and/or the cytotoxic activity of NK cells. These two parameters can easily be measured using techniques which are known to the skilled person and illustrated in the examples. Generally, the activation of the invention is not accompanied by a large increase in NK cell proliferation, all populations together, but could induce proliferation of a sub-population thereof. In contrast, this activation is accompanied by a significant increase in the survival of NK cells in vitro. More particularly, NK cell the activation within the context of the invention is independent of the use of conventional cytokines. The term "activated" NK cells as used within the context of the invention designates NK cells with at least one of the properties mentioned above.

The NK cell activation method of the invention can be carried out in vitro, ex vivo or directly in vivo.

NK Activation in the Presence of Dendritic Cells

In a first particular implementation, the method of the invention comprises activation of NK cells in vitro or ex vivo by co-culture of NK cells with mature or immature, autologous or allogenic, preferably triggered, dendritic cells.

In this first implementation of the method of the invention, NK cells are co-cultures with dendritic cells. In this implementation, the dendritic cells used can either be autologous (i.e., originating from the same individual as the NK cells), or allogenic (i.e., originating from another individual from the same species). The results shown in the examples demonstrate that NK cell activation is not significantly affected by the allogenic nature of the dendritic cells. This has the particularly advantageous effect of enabling "universal" banks of dendritic cells to be used to activate the NK cells. As described below, such banks can be constituted, for example, by modifying dendritic cells to render them immortal. In this respect, different lines of dendritic cells can be used to carry out the present invention, preferably established from immature human dendritic cells.

Prior to their use, it is possible to pre-treat the dendritic cells to improve their properties or to render them compatible with pharmaceutical use. Thus the dendritic cells can be irradiated prior to their use to activate NK cells. Such irradiation can completely eliminate any risk of cancer associated with certain populations of dendritic cells such as immortalised dendritic cells. Pre-treatment by irradiation can be particularly desirable when the dendritic cells or co-cultures are used in vivo. A further pre-treatment for dendritic cells can consist of incubation in the presence of dendritic cell stimulation factors (for example cytokines, chemokines, heat shock protein), to improve their NK cell stimulation activity or to trigger the production of dexosomes.

Preparation and Use of Triggered Dendritic Cells

A particularly advantageous treatment for dendritic cells comprises treating the cells in the presence of a triggering medium. The present invention describes the production and characterisation of a novel population of dendritic cells with greatly improved NK cell stimulation capacities. These "triggered" dendritic cells, the preparation thereof and the uses thereof constitute a further aspect of the present invention.

The term "triggering" as used in the context of the present invention means bringing dendritic cells into the presence of a signal, which is different from modulating their differentiation stage, which induces a large capacity for stimulating NK cells in the dendritic cells. The "triggering medium" can thus comprise any substance, generally a biological substance, which can provide dendritic cells with a signal inducing a high capacity to stimulate NK cells. In the present application, treated dendritic cells are also designated "triggered" dendritic cells (for "tDC").

In a particular aspect, the invention thus concerns a method for treating dendritic cells comprising bringing the dendritic cells into contact with a triggering medium to improve (or cause) their capacity to stimulate NK cells.

In a still further aspect, the invention provides a medium for triggering dendritic cells, i.e., a medium for improving (or causing) the capacity of dendritic cells to stimulate NK cells.

A suitable triggering medium for the present invention comprises, for example, cells which can provide dendritic cells with the appropriate signal, a preparation derived from such cells, a factor derived from such cells, or any substance, preferably biological, which can trigger dendritic cells.

Advantageously, the triggering medium further comprises growth factors and/or cytokines, in particular GM-CSF and/or interleukin-4 and, if necessary, constituents of a mammalian cell culture medium (serum, vitamins, amino acids, etc. . . . ).

Particularly included among the cells which can be used to trigger dendritic cells is the extracellular matrix, in particular stromal, endothelial or fibroblastic cells. These cells, more particularly when they are in the division phase, can trigger dendritic cells. The same is true for certain tumour cells such as mastocytoma cells. One particular implementation of the invention comprises using fibroblasts for triggering. The Applicant has demonstrated that fibroblasts enable dendritic cells to stimulate NK cells with much higher efficiency. In this respect, immortalised fibroblasts, transformed lines, or primary cultures, which may or may not be activated, can be used, prepared in advance or extemporaneously, etc. Preferably, cells used for DC-triggering cell co-culture are in division or capable of dividing. Examples of suitable fibroblast lines are NIH3T3, L-929, MRC5 and TIB80.

In order to carry out this method, the fibroblasts (or other cells) used can be autologous, allogenic or xenogenic as regards the dendritic cells. Surprisingly, the results shown in the examples demonstrate that human dendritic cells can be triggered by fibroblasts of a different species, in particular by murine fibroblasts. In this implementation (in vitro co-culture), triggering (treatment) can be carried out using a DC/cell ratio of about 0.1 to 100, preferably 0.5 to 10, in particular 1 to 5. It should be understood that this ratio can be adjusted by the skilled person. Further in this implementation, irradiated cells are preferably used (for example between 2000 and 8000 rads).

Instead of intact cells, the triggering medium can also be a preparation or a factor derived therefrom. Thus it is possible to use a supernatant, a lysate, an acellular preparation, or an isolated and/or purified factor, etc. The results shown in the examples demonstrate in particular that a fibroblast culture supernatant can trigger dendritic cells, i.e., can render them capable of activating resting NK cells very effectively (more rapidly). In this implementation, for example, about 1 to 20 ml of a cell supernatant (for example from fibroblasts) can be used per $10^6$ dendritic cells, in a final volume of about 30 ml. It is thus possible to use a supernatant diluted by 1.5 to 30 times, preferably 2 to 5 times. These conditions can, of course, be adapted by the skilled person depending on the cell populations used. Further, the activity described above for the culture supernatant demonstrates the existence of a soluble factor which is responsible for or sufficient to carry out the triggering, secreted by the cells, in particular fibroblasts. A further triggering medium thus comprises, for example, a supernatant concentrate/filtrate, more particular a soluble factor as mentioned above, in an isolated and/or purified and/or recombinant form. Thus the triggering medium can be the soluble factor described above or a recombinant cell expressing this factor. It is also possible to use any other substance, in particular, a biological substance, to trigger dendritic cells to activate NK cells.

Generally, triggering is carried out by incubating dendritic cells in the presence of a triggering medium for a period of 15 to 72 hours, usually about 20 to 48 hours. The "triggered" state of the dendritic cells does not modify their immunological phenotype. Thus immature dendritic cells remain immature after triggering (expression of HLA-DR, CD40, CD80, CD86, CD83, CD1a). The "triggered" stage can be demonstrated in a number of ways, generally by testing the capacity of the cells to activate NK cells in vitro, as described in the examples, or by measuring the soluble triggering factor in the culture supernatant.

Further in the context of activating NK cells, dendritic cells can be triggered prior to incubation in the presence of NK cells, or concomitantly therewith.

As indicated above, the present invention also concerns a population of dendritic cells termed triggered dendritic cells. In this respect, in a further aspect the invention also provides a composition comprising triggered dendritic cells, in particular human dendritic cells, which are mature or immature, i.e., dendritic cells with an increased capacity to stimulate NK cells, in particular by a factor of at least two with respect to non triggered dendritic cells.

More particularly, the triggered dendritic cells of the invention can be defined as activating resting NK cells and in that they can be obtained by treating mature or immature dendritic cells in the presence of a triggering factor or medium as defined above, preferably comprising a culture of extracellular matrix cells or a supernatant of such cells.

DC-NK Co-cultures

In order to carry out the NK cell activation method of the invention, the dendritic cells used can be mature dendritic cells (in particular in a murine system) or, preferably, immature dendritic cells (in human and murine systems). As will be shown in the examples, dendritic cells can activate NK cells at any stage in their maturity, in particular after triggering as described above.

To increase the efficacy of activation, certain parameters should advantageously be satisfied such as the ratio of NK cells to dendritic cells and/or the co-incubation time. Thus the experiments carried out by the Applicant have demonstrated that the best performances of the in vitro or ex vivo activation method were obtained when the initial NK cell to dendritic cell ratio was in the range 0.01 to 10, preferably in the range 0.05 to 5. It should be understood that the skilled person is free to adapt this ratio depending on the cell population used, taking into account the stifling effect of NK cells which can be observed when the quantity of dendritic cells is too high, and the low level of activation which can be observed when the number of dendritic cells is too low. Particularly preferred conditions are those in which the initial ratio of NK cells to dendritic cells is in the range 0.1 to 1, more preferably in the range about 0.1 to 0.5.

The co-culture time can also be adapted by the skilled person as a function of the cell populations used and in particular of the maturation stage and triggering of the dendritic cells. In general, optimal NK cell activation is observed after co-culture for a period in the range about 18 to 48 hours. Preferably, when the dendritic cells are triggered as described above, resting NK cells are activated after a co-culture period of less than 20 hours. The co-culture periods indicated above can in particular produce the best combination between the proportion of activated NK cells and the proportion of viable cells. It should be noted in this respect that, during the dendritic cell activation period, no significant global NK cell proliferation is observed (a factor of about 2) not excluding isolated and particular proliferation of an NK sub-population. Further, particularly unexpectedly, it appears that dendritic cells also exert a positive effect on the survival of cultured NK cells. Because of this, the method of the invention can produce activated NK cells without the need to use cytokines, and with improved yields. Similarly, NK cells increase the survival of mature DC.

NK cell activation and triggering dendritic cells in vitro can be carried out in any suitable cell culture apparatus, preferably under sterile conditions. In particular, they may be plates, culture dishes, flasks, pouches, etc. Co-culture is carried out in any medium suitable for culturing dendritic cells and NK cells. More generally, it may be a commercially available culture medium for culturing mammalian cells, such as RPMI medium, DMEM medium, IMDM medium or GBEA media (AIMV, X-VIVO), etc.

In a first particular variant of the method of the invention, NK cells are activated in vitro or ex vivo by co-culture of mature dendritic cells with NK cells.

In a typical experiment, dendritic cells derived from bone marrow by treatment with GM-CSF+IL-4, matured in LPS, or cells of an established dendritic cell line in the mature state, are re-suspended in their culture medium in a concentration of 1 million/ml. They are then cultured on plates or any other appropriate apparatus. Fresh resting NK cells (autologous or allogenic), obtained after the adhesion step, are re-suspended in a suitable medium (supplemented RPMI medium, for example) in a concentration of 1 million/ml. They are then added to the plate containing the dendritic cells such that the initial NK:DC ratio is about 0.1 to 0.3. The co-culture is recovered after about 18–36 hours. The activated character of the NK cells is monitored by measuring the IFNγ production in the supernatant and measuring the cytotoxicity against target cells. The NK cells are also counted (for example using trypan blue) and analysed (for example by flux cytometry) for expression of characteristic markers (such as NK1.1D×5 or asialo-GM1 in the mouse) and to evaluate the cell mortality.

In a further particular variation of the method of the invention, in vitro or ex vivo activation of NK cells is carried out by co-culture of immature dendritic cells with NK cells.

In a typical experiment, the cells are treated in identical manner to those described above, but they are not incubated in a maturation medium, so as to keep the dendritic cells at an immature stage. In this implementation, co-culture is advantageously maintained for at least 36–72 hours to provide optimal NK activation. The activated NK cells can then be analysed and monitored as described above.

In a preferred implementation of the method of the invention, NK cells are activated in vitro or ex vivo by co-culture of triggered dendritic cells with NK cells. In this implementation, a co-culture of less than 20 hours is sufficient to enable optimal NK cell activation. The activated NK cells can then be analysed and monitored as described above. More preferably, they are immature dendritic cells pre-incubated in the presence of a triggering medium. More preferably still, they are immature dendritic cells pre-incubated in the presence of fibroblasts or a fibroblast supernatant or a proteic factor produced by fibroblasts.

When the NK cells have been activated in this manner, either the NK cells can be separated from the dendritic cells, or the NK cell: dendritic cell co-culture can be harvested directly. In this respect, the invention also provides a composition comprising NK cells and dendritic cells, in particular a NK cell: dendritic cell co-culture. As indicated above, they are advantageously activated NK cells. Further, they may be mature or immature dendritic cells, preferably triggered. Finally, in these compositions of the invention, the cell populations are preferably autologous, i.e., from the same organism. These compositions are advantageously constituted by isolated cell populations, i.e., each of the two cell populations is composed of at least 10%, preferably at least 30%, in particular at least 50%, of the corresponding cell type (NK or dendritic). Further, preferred compositions of the invention generally comprise at least 10%, preferably 20% to 60%, more preferably 30% to 60% of NK cells, and at least 40%, preferably 40% to 80%, of dendritic cells. The invention also concerns any composition comprising activated NK cells as described in the present application. The compositions of the invention can be packaged in any suitable apparatus such as pouches, flasks, ampules, syringes, vials, etc., and can be (cold) stored or used extemporaneously, as described below. Advantageously, these compositions comprise $10^4$ to $10^9$ NK cells, preferably about $10^6$ to $10^8$ (in particular for administration to humans) or $10^5$ to $10^6$ (in particular for administration to mice).

NK Cell Activation in the Presence of a Preparation Derived from DC

In a further implementation, the method of the invention comprises in vitro, ex vivo or in vivo activation of NK cells by bringing NK cells into the presence of a preparation derived from dendritic cells. The preparation derived from dendritic cells can be any preparation or membranous fraction of dendritic cells, a cell lysate of dendritic cells, membranous vesicles of dendritic cells, or the stimulation factor derived from dendritic cells, in an isolated, enriched or purified form.

As illustrated in the present application, the NK cells can be activated not only in the presence of intact dendritic cells, but also in the presence of membrane preparations thereof, in particular of membranous vesicles (for example dexosomes), or in the presence of a proteic stimulation factor.

In a first variation, the method of the invention comprises in vitro, ex vivo or in vivo activation of NK cells by bringing NK cells into the presence of membranous vesicles produced by dendritic cells. In this respect, dendritic cells have been shown to produce membranous vesicles, with a diameter which is generally in the range 50 to 100 nm, termed dexosomes (French patent applications FR 97 09007, FR 98 01437). The present invention shows that these vesicles are also endowed with a NK cell stimulation activity. In particular, the present application demonstrates that the dexosomes produced from human or murine dendritic cells can activate murine NK cells. Further, the results obtained show that this activation is observed even with dexosomes produced by non triggered dendritic cells.

To implement this variation, dexosomes produced from immature dendritic cells are preferably used, preferably autologous or allogenic. For in vitro or ex vivo applications, the dexosomes are preferably used in a concentration range of 10 to 100 μg of exosomal proteins per million NK cells. The quantity of exosomal proteins can readily be determined by the skilled person, for example using the Bradford test (Annal. Biochem. 72 (1976) 248). More preferably, dexosomes are used in a concentration of 15 µg/$10^6$ NK cells or more, more preferably still 20 µg/$10^6$ NK cells or more. It should be noted that these concentrations can be adapted by the skilled person, and can be transposed to in vivo use. In particular, for in vivo use, exosome doses of over 50 or 100 µg/injection can be used.

The dexosomes can be prepared using techniques described in French patent applications FR 97 09007 and FR 98 01437, for example, which are illustrated in the examples. In brief, dendritic cells are cultivated, preferably to the immature stage, preferably in a medium which encourages dexosome production. The dexosomes are then isolated by methods such as centrifugation (in particular differential centrifugation at 70 000 g), or any other technique which is known to the skilled person. The dexosomes are then isolated, divided into aliquots and preserved or used extemporaneously to stimulate NK cells.

In a further variation, the method of the invention comprises in vitro, ex vivo or in vivo NK cell activation by bringing the NK cells into the presence of a stimulation factor originating from dendritic cells, in particular from triggered dendritic cells.

The results shown in the present application illustrate the specific nature of the activation of NK cells by dendritic cells, and thus indicate the involvement of one or more factors produced or expressed by dendritic cells in carrying out this effect. In this respect, the present application also shows, in a "transwell" experiment, that intercellular contact between NK cells and dendritic cells or a membranous preparation derived therefrom appears to be necessary for activation. These results clearly indicate the existence of a NK cell stimulation factor expressed (on the surface) by dendritic cells and dexosomes, responsible for or at least necessary for NK cell activation. This (membranous) (co-) stimulation factor, or any acellular preparation containing it, or any derivative or recombinant forms of this factor and the corresponding nucleic acids, can thus also be used in vitro or in vivo to activate NK cells, in particular for anti-tumoral or anti-viral immunisation applications. This factor can also be blocked using a competitor, specific or anti-sense antibodies, for certain situations such as graft versus host disease.

In a further aspect, the present invention provides a composition comprising a NK cell stimulation factor derived from DC, in particular a membrane factor involved in the activation of NK cells by dendritic cells. The term "involved" means that this factor is necessary or at least participates in the activation of NK cells by dendritic cells. This composition is, for example, composed of an acellular extract of dendritic cells comprising said factor, or membranous vesicles or any isolated or purified form of this factor. The term "derived" indicates that this factor, which is essentially proteic in nature, can in particular be purified by different isolation methods which are well known to the skilled person, such as cell lysis, followed by different centrifugation steps (differential centrifugation, ultracentrifugation, etc), and/or chromatography, electrophoresis, the production of neutralising antibodies and their use for isolation by immuno-affinity, etc. Each of these techniques, used alone or in combination(s), can be used to isolate the stimulation factor involved in activation, following the different purification steps with a NK cell activation test as described in the present application. A further approach for identifying this factor resides in the use of a dendritic cell DNA bank, and in the search for clones endowed with activity or capable of complementing dendritic cell mutants which are deficient in this activity. From this point of view, differential DNA banks (by subtraction between a triggered dendritic cell and a non triggered dendritic cell) can be established.

More generally, the present invention describes a method for preparing factors which can stimulate NK cells, involving inter-membrane contact between NK cells and a test composition. More particularly, the invention concerns a method for identifying and/or preparing an NK cell stimulation factor, comprising bringing a biological substance comprising a membranous fraction into contact with a preparation of NK cells, demonstrating NK cell activation, and isolating the activating factor present in the biological substance. More preferably, the biological substance comprising a membranous fraction is a dendritic cell, a sub-cellular dendritic cell preparation (in particular a membranous vesicle), or a cell transformed by a nucleic acid coding a polypeptide product. Thus it may be mammalian cells (for example COS cells) transformed by a DNA bank of human origin, in particular a dendritic cell DNA bank. Clones inducing stimulation of NK cell activity are selected, and the insert they contain is isolated, purified and characterised. This method thus enables any nucleic acid coding a NK cell stimulation factor to be cloned. The nucleic acid obtained can be modified, introduced into an expression vector and used in a method for producing a proteic stimulation factor.

The invention also concerns a method for identifying and/or preparing a NK cell stimulation factor, comprising bringing a biological substance comprising a membranous fraction into contact with a NK cell population, demonstrating NK cell activation, and isolating an activation factor present in the biological substance.

A particular composition of the present invention thus comprises a NK cell stimulation factor derived from DC, which is essentially proteic in nature, which can be obtained from the membranes of mature dendritic cells or membraneous vesicles produced by immature dendritic cells.

A more particular composition comprises a factor with an essentially proteic nature which can be obtained from exosomes produced by immature human dendritic cells, and which can stimulate secretion of gamma interferon by resting NK cells.

Further, the term "derived" also indicates that the compositions of the invention can comprise any variant or recombinant form of the stimulation factor identified above, in particular expressed from a cultured recombinant cell, such as a yeast or a mammalian cell.

In this respect, the compositions of the invention can also contain any nucleic acid coding for the stimulating membrane factor for dendritic cells (in particular triggered) as described above. This nucleic acid can be obtained using any technique which is known to the skilled person, in particular from a DNA bank of triggered dendritic cells. Finally, the compositions of the invention can also contain any other NK cell co-stimulation factor, in particular any lymphokine or cytokine which can activate NK cells in combination with the stimulation factor described above.

In a particular implementation, the invention thus comprises a process for in vitro, ex vivo or in vivo activation of NK cells by bringing NK cells into contact with a stimulation factor derived from dendritic cells.

The invention thus also concerns the use of a stimulation factor as described above to prepare a composition for increasing the cytolytic activity of NK cells or the in vivo production of IFNγ and/or TNFα.

The invention also concerns the use of a stimulation factor as described above to prepare a composition intended to increase the natural immunity of an organism.

The invention further concerns a stimulation factor as described above to increase the cytolytic activity of NK cells for the in vitro or ex vivo production of IFNγ and/or TNFα.

The invention still further concerns a process for negative control of in vitro or in vivo NK cell activation comprising bringing NK cells into the presence of a compound which can interfere with (i.e., at least partially inhibit) the interaction between NK cells and dendritic cells. Such a compound can, for example, comprise a soluble form (soluble receptor) or any other stimulation factor fragment (the extracellular domain, in particular the binding site), an analogue, an antagonist, a competitor, an antibody or an antibody fragment, an anti-sense, etc. Such a compound can be identified and/or characterised in a screening test using a stimulation factor as described above, or in any functional direct or indirect NK cell activation test.

In this respect, the invention also concerns a method of identifying and/or characterising a compound capable of inhibiting NK cell activation, comprising incubating a test compound or a composition comprising one or more test compounds with resting NK cells and dendritic cells, preferably triggered dendritic cells, or dexosomes, or a NK cell stimulation factor as described above, measuring the NK cell activation, and selecting compounds/compositions which are capable of inhibiting (i.e., reducing) NK cell activation, compared with a control experiment carried out in the absence of test compound/composition. The invention thus also concerns the use of compounds which inhibit this activation of NK cells by dendritic cells, as a drug or pharmaceutical composition for external (ex vivo) or internal (in vivo) use.

In this respect, the invention still further concerns any compound which can interfere with the interaction between dendritic cells and NK cells and thus at least partially inhibit contact between a dendritic cell (or a dexosome) and a NK cell. As described above, this compound can be a neutralising antibody, a competitive ligand, an analogue, a stimulation factor fragment or derivative, any chemical molecule etc. The invention also concerns the use of such a compound for in vivo or in vitro control of NK activation, in particular in applications such as graft rejection prevention, and GVHD. Further, the invention also concerns the use of "tolerogen" phenotype dendritic cells such as GC-DC, described by Grouard et al., (Nature 384, 364–367, 1996) or a product derived from tolerogenic dendritic cells to inhibit NK cell activation.

NK Activation by Increasing DC in vivo

In a further implementation of the invention, the method of the invention comprises in vivo activation of NK cells by increasing the level of dendritic cells in vivo. This in vivo increase can exert an in situ activation of NK cells and can thus reinforce the natural immunity of an organism, in particular against tumour or infected cells.

Dendritic cells can be increased in vivo by in vivo administration of dendritic cells, optionally triggered (passive transfer) or also by in vivo administration of one or more growth factors and/or triggering factors for dendritic cells, possibly in association. Administration can be carried out by injection, for example, preferably by subcutaneous or systemic injection. Injection is preferably a local or regional injection, in particular into the site or close to the site to be treated, in particular close to a tumour. The results shown in the examples demonstrate in particular that administration by subcutaneous or intravenous injection of immature or mature, allogenic or autologous dendritic cells in vivo, to the tumour site, can retard the growth of negative class I MHC tumours. Injections are generally carried out on the basis of cell doses of $10^4$ to $10^9$ dendritic cells, preferably in the range $10^5$ to $10^7$ inclusive. Further, the skilled person can adapt the injection protocol to the situation (preventative, curative, isolated tumours, metastases, extended or local infection, etc.). Thus it is possible to carry out passive transfer of dendritic cells by repeated administration, for example 1 or 2 administrations per week, over several months.

In vivo increase of dendritic cells can also be carried out by in vivo injection of dendritic cell growth factor. Such factors are, for example, the compound Flt3L (hereinafter termed "FL"), described by Lyman S. D. et al., (Blood 83, 2795–2801, 1994, "Cloning of the human homologue of the murine Flt3L: A growth factor for early hematopoietic progenitor cells) and Maraskovsky E. et al., (J. Exp. Med. 184, 1953–1962, 1996) or GM-CSF, for example. The examples show that in vivo stimulation of natural immunity (and thus the activity of NK cells) is obtained after daily injection of Flt3L. The results shown also demonstrate that this injection produced an increase in the absolute number of in situ NK cells, and induced anti-tumoral effects, which were dependent on lymphoid dendritic cells and the B7/CD28 interaction and an IFNγ in vivo. As indicated below, the FL compound can also advantageously be associated with the dendritic cell triggering factor.

This implementation thus constitutes a further particularly effective approach to increasing the cytolytic activity of NK cells in vivo. This approach can advantageously be associated with in vivo co-administration of a NK cell growth factor.

The invention thus also concerns the use of dendritic cells for the preparation of a composition intended to activate NK cells in vivo. The invention also concerns the use of dendritic cells to prepare a composition intended to activate the cytolytic activity of NK cells in vivo and the production of IFNγ and/or TNFα by activated NK cells. As indicated above, the dendritic cells used are mature or immature, autologous or allogenic cells, in particular triggered cells. Further, they may also be dendritic cells sensitised to one or more antigens.

The invention also concerns a dendritic cell growth factor for the preparation of a composition intended to activate NK cells in vivo and for the preparation of a composition intended to activate the cytolytic activity of NK cells in vivo. The growth factor is preferably FL. The growth factor can advantageously be associated with the dendritic cell triggering factor in vivo.

The invention also concerns the use of a proteic factor, or more generally a biological factor, for triggering dendritic cells to directly activate NK cells in vivo, optionally in association with a dendritic cell growth factor and/or one or more chemokines or cytokines.

In a particular implementation of the method of the invention, the number of dendritic cells is increased in vivo either by in vivo administration, under the conditions described above, of dendritic cells triggered in vivo as described above (passive transfer) or also by in vivo administration of one or more dendritic cell growth factors and one or more dendritic cell triggering factors. This implementation can improve the efficacy of NK cell activation in vivo, provided that the cells or compounds administered can produce high levels of triggered dendritic cells in vivo.

In this respect, the invention also concerns a composition comprising at least one dendritic cell triggering factor and a dendritic cell growth factor, as described above, for their simultaneous, separate or time delayed use. More particularly, such a composition comprises FL and a preparation derived from fibroblasts comprising a soluble triggering factor. More particularly still, it comprises a recombinant soluble factor. The invention also concerns the use of such a composition for preparing a composition intended to activate NK cells in vivo and for preparing a composition intended to activate the cytolytic activity of NK cells in vivo. For use, these compounds can be packaged in any suitable medium (saline solutions, buffers, etc.), preferably isotonic, and in any apparatus known to the skilled person (ampule, flask, tube, syringe, pouch, etc.).

Preparation of Resting NK Cells

NK cells can be obtained for the present invention using different techniques which are known to the skilled person. More particularly, these cells can be obtained by different isolation and enrichment methods using peripheral blood mononuclear cells (lymphoprep, leucapheresis, etc.). Thus these cells can be prepared by Percoll density gradients (Timonen et al., J. Immunol. Methods 51 (1982) 269), by negative depletion methods (Zarling et al., J. Immunol. 127 (1981) 2575) or by FACS sorting methods (Lanier et al., J. Immunol. 131 (1983) 1789). These cells can also be isolated by column immunoadsorption using an avidine-biotin system (Handgretinger et al., J. Clin. Lab. Anal. 8 (1994) 443) or by immunoselection using microbeads grafted with antibodies (Geiselhart et al., Nat. Immun. 15 (1996–97) 227). It is also possible to use combinations of these different techniques, optionally combined with plastic adherence methods.

These different techniques can produce cell populations which are highly enriched in resting NK cells, preferably comprising more than 70% of resting NK cells. More preferably, the NK cell populations used to carry out the invention generally comprise more than 30% of NK cells, advantageously more than 50%. The purity of the cell populations can be improved if necessary using specific antibodies such as anti-CD56 antibodies and/or anti-CD16 antibodies and/or anti-CD3 antibodies (depletion).

The NK cells can be preserved in a culture medium in a frozen form for subsequent use. Advantageously, the NK cells are prepared extemporaneously, i.e., they are used for activation after production.

Preparation of Dendritic Cells

The dendritic cells used in the present invention can be prepared using different techniques. These cells can be immature or mature, autologous or allogenic, naïve or sensitised to one or more particular antigens, preferably triggered. Further, the dendritic cells used can be cell cultures enriched in dendritic cells, or cell cultures comprising essentially dendritic cells. Advantageously, they are human dendritic cells.

The preparation of dendritic cells has been well documented in the literature. Thus it is known that these cells can be prepared from hematopoietic stem cells or from monocyte precursors, or they can be directly isolated in a differentiated form (review by Hart, Blood 90 (1997) 3245).

The production of dendritic cells from stem cells is illustrated, for example, by Inaba et al., (J. Exp. Med. 176 (1992) 1693) for the mouse, and by Caux et al., (Nature 360 (1992) 258) or Bernhard et al. (Cancer Res. 55 (1995) 1099) for man. These studies show that dendritic cells can be produced by culturing bone marrow in the presence of Granulocyte-Macrophage Colony Stimulation Factor (GM-CSF) or, more precisely, from hematopoietic stem cells (CD34+) by culture in the presence of a combination of cytokines (GM-CSF+TNFα±IL-3 and IL-4 or CD40L).

The production of dendritic cells from monocyte precursors is illustrated, for example, by Romani et al. (J. Exp. Med. 180 (1994) 83), Sallusto et al. (J. Exp. Med. 179 (1994) 1109), Inaba et al. (J. Exp. Med. 175 (1992) 1157) or Jansen et al. (J. Exp. Med. 170 (1989) 577). These methodologies are essentially based on removing mononuclear cells from blood and culturing them in the presence of different combinations of cytokines. A particular method consists of treating monocyte blood precursors in the presence of combinations of cytokines such as interleukin-4+GM-CSF or interleukin-13+GM-CSF, for example. This technique is also illustrated by Mayordomo et al., 1995 (rat). Further, it is also possible to treat monocyte precursors with pharmacological cell differentiation agents, such as calcium channel activators or CD40L directly.

A further approach for producing dendritic cells consists of isolating dendritic cells which have already differentiated from biological samples. This approach has been described, for example, by Hsu et al. (Nature Medicine 2 (1996) 52). The methodology described by this team essentially consists of harvesting samples of peripheral blood and treating them with different gradients and centrifugations to extract dendritic cells.

The preferred methodology used in the present invention is based on the production of dendritic cells from monocyte precursors or bone marrow. These methodologies are illustrated in the examples. More particularly, the present invention preferably uses dendritic cells obtained by treating monocyte precursors (contained in blood or marrow) in the presence of a GM-CSF+IL-4 or GM-CSF+IL-13 combination.

As indicated above, to implement the present invention, it is possible to use a population of dendritic cells comprising immature and/or mature dendritic cells. Advantageously, a population of dendritic cells principally composed (i.e., at least 60%, preferably 70%) of immature dendritic cells, preferably triggered, is used. The immature state of dendritic cells corresponds to an early stage in their development, in which they have a high endocytic activity and express low levels of class I and II MHC molecules and lymphocytary co-simulation molecules on their surface.

Further, within the context of the present invention it is also possible to use dendritic cell lines. They may be immortalised dendritic cells produced, for example, by introducing an oncogene into dendritic cells. A murine example of such a line may be the following lines described in the prior art: D1 line (Winzler et al., J. Exp. Med. 185, 317–328, 1997), XS line (A. Takashima et al., J. Immunol 1995; Vol 154: 5128–5135), tsDC line (Volkmann et al., Eur. J. Immunol. 26: 2565–72, 1996). The importance of using dendritic cell lines is based on the constitution of "universal" cell banks used commercially to activate populations of allogenic NK cells from different subjects. In this implementation, the line is preferably maintained in 30% triggering medium or with an optimum concentration of triggering factor.

When dendritic cells are prepared, they can be maintained in culture, further purified, stored or used directly to implement the present invention (in vitro, ex vivo or in vivo activation of NK cells, production of acellular extracts, dexosomes, producing a membrane stimulation factor, etc). Further, prior to their use to activate NK cells, the prepared dendritic cells can be sensitised to an antigen or a group of antigens. The presence of antigenic moieties on the dendritic cell surface can improve (by cross-priming) or inhibit (in a KIR mode) their immunogenic activity (acquired immunity) in particular in in vivo use.

In this respect, different techniques can be used to sensitise dendritic cells to antigens. In particular, these techniques are:

Bringing dendritic cells into contact with antigenic peptides ("peptide pulsing"). This approach consists of incubating dendritic cells, for a variable period (generally 30 minutes to about 5 hours) with one or more antigenic peptides, i.e., with a peptide from an antigen, such as could result from treating said antigen with a cell presenting the antigen. This type of approach has been described, for example, for antigenic peptides of the HIV virus, influenza virus or HPV or for peptides derived from Muc-1, Mart, Her2/Neu antigens, for example (Macatonia et al., J. Exp. Med. 169 (1989) 1255; Takahashi et al., Int. Immunol. 5 (1993) 849; Porgador and Gilboa, J. Exp. Med. 182 (1995) 255; Ossevoort et al., J. Immunother. 18 (1995) 85; Mayordomo et al., cited above; Mehta-Damani et al., J. Immunol. (1994) 996). It is also possible to incubate dendritic cells with an acidic peptide eluate of a tumoral cell using the methodology described by Zitvogel et al. (1996, cited above).

Bringing dendritic cells into contact with one or more antigens ("antigen pulsing"). This approach consists of incubating dendritic cells not with one or more antigenic peptides, but with the intact antigens. The importance of this technique is based on the fact that the antigen will be transformed into antigenic peptides by natural mechanisms in the dendritic cells, such that the resulting antigenic peptides presented by the dendritic cell should provide better immunogenicity. This approach has been illustrated, for example, by Inaba et al. (J. Exp. Med. 172 (1990) 631) or Hsu et al., (Nature Medicine 2 (1996) 52).

Bringing dendritic cells into contact with one or more antigenic proteic complexes. This approach is similar to the preceding approach but can improve the efficiency of transformation and/or of presentation of the antigen. In particular, the antigen can be used in a soluble form or complexed with targeting elements, in particular to target membranous receptors such as mannose receptors or immunoglobulin receptors (RFc) (immune complexes). It is also possible to render the antigen particulate so as to improve its penetration or its phagocytosis by the cells.

Bringing dendritic cells into contact with cells (hybridoma-like fusion) or membranes, lysates or sonicates of cells expressing antigens or antigenic peptides. This technique is based on direct transfer of antigens or antigenic peptides by fusion of cells or cell membranes. This approach has been illustrated, for example, by fusion between dendritic cells and membranes of tumour cells (Zou et al., Cancer Immunol. Immunother. 15 (1992) 1, and Gilboa, cited above).

Bringing dendritic cells into contact with membranous vesicles containing antigens of antigenic peptides (in particular exosomes of tumour cells such as those described above). This approach for sensitising dendritic cells using exosomes, such as is shown in the present invention, is particularly advantageous in that it does not require a knowledge of particular antigens and where the loaded antigenic peptides are in a native conformation. The technology has been illustrated in the examples.

Bringing dendritic cells into contact with liposomes containing antigens or antigenic peptides (Nair et al., J. Exp. Med. 175 (1992) 609).

Bringing dendritic cells into contact with RNAs coding for antigens or antigenic peptides, (see Boczkowsky et al., 1996, cited above).

Bringing dendritic cells into contact with DNAs coding for antigens or antigenic peptides or nucleic acid sequences coupled to proteic antigens (optionally incorporated into plasmid, viral or chemical type vectors). Thus one method of sensitising dendritic cells consists, for example, of infecting dendritic cells with a virus against which protection is desired. This has been described, for example, for the influenza virus (Bhardwaj et al., J. Clin. Invest. 94 (1994) 797; Macatonia et al., cited above). A further approach consists of delivering, using a virus or other nucleic acid transfer vectors, a DNA coding for the antigens or antigenic peptides of interest. Such an approach has been illustrated, for example, by Arthur et al., (Cancer Gene Therapy, 1995) or by Alijagie et al. (Eur. J. Immunol. 25 (1995) 3100). Certain viruses such as adenovirus, AAV or retroviruses appear to be able to be used to this end, to deliver a nucleic acid into a dendritic cell.

Applications

The invention also concerns the use of the methods, cells and compositions described above, in particular in the fields of immunology, immunotherapy or medical biotechnology. As indicated above, these uses are multifold, both in vitro and in vivo, to control the activity of NK cells. Such applications are in particular the treatment of different disorders such as cancers of infectious diseases, in particular viral diseases, or other pathogens, autoimmune diseases, disorders linked to transplantation (graft rejection, GVHD), congenital disorders (deficits in the interferon receptor or interleukin-12 receptor, for example), etc. The methods, cells and compositions of the invention are in particular used to retard the growth, or even to suppress tumours (in particular tumours with low expression of class I MHC molecules) or other pathological cells. For this type of application, as indicated above, cell compositions (activated NK cells, NK/DC co-cultures or dendritic cells) can be administered loco-regionally, preferably by subcutaneous or systemic injection. The cell doses are indicated above and in the experimental section below. The invention can also be used in vitro to treat cell preparations, in particular to destroy cells sensitive to NK cells. The invention can also be used in combination or as an adjuvant for immunisations based on the development of a specific cytotoxic T lymphocyte antigen activity. The invention further concerns the use of dendritic cells or a membranous factor of dendritic cells to increase survival of NK lymphocyte populations in vitro, ex vivo or in vivo, and to increase, if necessary, the proliferation of NK lymphocyte sub-populations. The invention also concerns the use of NK cells or a membranous factor of NK cells to increase the survival rate of mature dendritic cells in vitro, ex vivo or in vivo.

Other advantages of the present invention will become apparent from the following examples which are given by way of illustration and are not limiting.

KEY TO FIGURES

FIG. 1: Immature dendritic cells stimulate NK activity in vitro.

Immature autologous dendritic cells derived from BALB/c mouse marrow, i.e., cultivated in GM-CSF and interleukin-4, were incubated for 24 hours in 30% L-929 fibroblast medium or were co-cultivated with irradiated L-929. After 24 hours, they were counted, re-suspended in conventional medium (GM-CSF+IL-4) and co-incubated for a period of 40 to 72 hours at a concentration of 1 million cells per ml in round bottom wells, in 96 well plates, with resting spleen cells (10–30% of which were NK), from the spleen of syngenic SCID BALB/c mice in the same concentration. The cytotoxicity against YAC and P815 target cells and the γ interferon release by NK cells were determined as described in the Method and Apparatus section.

FIG. 2: Mature dendritic cells directly stimulate NK activity in vitro.

(a) Mature dendritic cells from the spleen (derived from the spleen of C57BL/6 animals) very clearly stimulated the cytolytic activity of NK cells. Dendritic cells, incubated in the presence of L-929 supernatant (30%) then for 24 hours in a medium containing TNFα, were co-cultivated with non-adherent mononuclear spleen cells from the B6-Rag-/- mouse or SCID mouse in a 1:1 ratio for 40 to 48 hours. Viable lymphocytes were tested against YAC-1 cells in a chromium 51 release test for 4 hours. The results are expressed as the specific lysis percentage at different effector cell/target cell ratios. These experiments were carried out 5 times with similar results.

(b) Mature spleen dendritic cells stimulated the production of γ interferon by NK cells. The supernatants from dendritic cells or syngenic or allogenic NK cells cultivated separately or together at different concentration ratios were collected after 48 to 72 hours and tested for the presence of murine γ interferon by ELISA. It should be noted that the NK:DC ratios corresponded to the ratio of the spleen cells of animals depleted in T/B/Mac (containing 10–30% of pure NK):DC. No trace of interferon γ was detected in the supernatant of NK cells or dendritic cells cultivated separately as controls.

Figure 3:
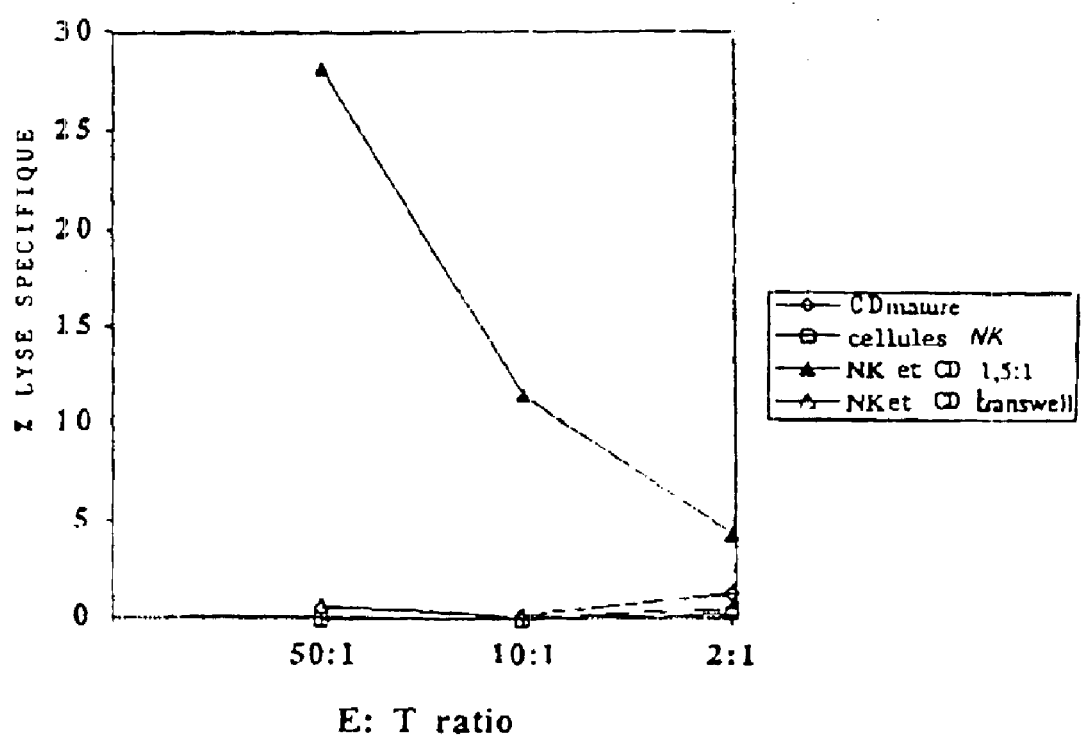

FIG. 3: Activation involves NK cell: dendritic cell contact

A study of the specific lysis of target cells (YAC-1) induced by NK cells activated in vitro by a dendritic cell line, either by co-culture (solid triangles), or using a transwell system in which the two cell populations are physically separated by a porous membrane (open triangles) and distanced from each other by 1 mm. The controls are represented by separately cultivated NK cells and dendritic cells.

Figure 4:
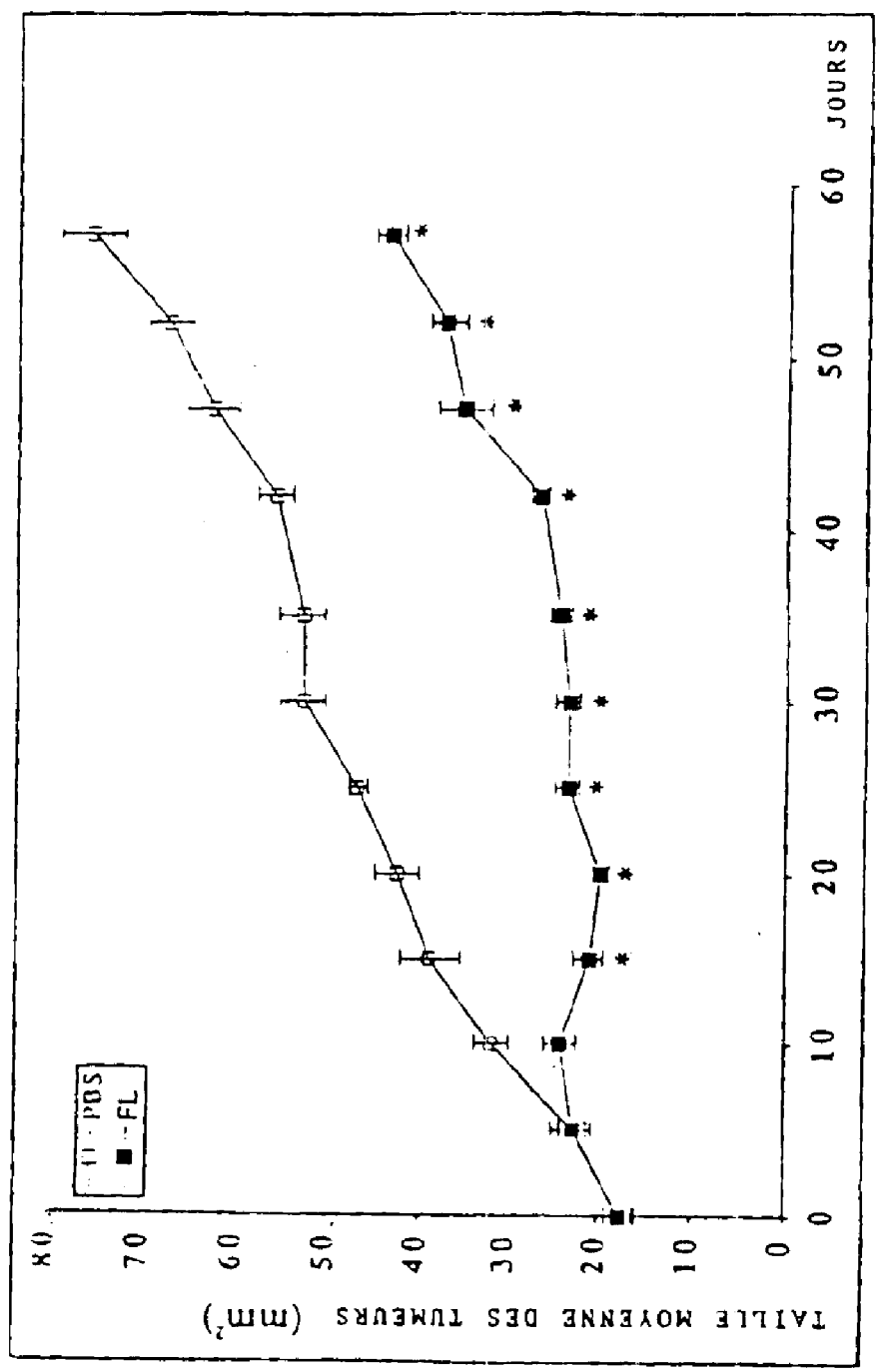

FIG. 4: Administration of FL in B6-nude mice with an AK7 tumour induces significant suppression of tumour growth.

10 μg of FL was administered daily over 20 days to B6-nude mice with a 20 day established mesotheliomal AK7 tumour. Tumour growth was checked twice a week for 60 days. The average sizes of the tumours for groups of 5 mice are shown in the Figure with the standard deviation. This experiment was repeated four times with similar suppression of tumour growth. Similar results are obtained with Rag2 B6-/-mice.

FIG. 5: Anti-tumoral effects induced by FL are dependent on NK cells (a) FL had no effect on B6-beige mice. 10 μg of FL was administered daily for 20 days to B6-beige mice with an established 20 day AK7 tumour. Tumour growth was monitored twice a week for 50 days. The average tumour size for groups of 5 mice is shown in the figure, with the standard deviation. This experiment was carried out twice with identical results.

(b) Co-administration of anti-NK-1.1 neutralising monoclonal antibodies at the same time as FL inhibited the anti-tumoral effect of FL. 300 μg per mouse of anti-NK1.1 antibody was co-administered daily to immunocompetent B6 mice with an established 20 day tumour at the same time as FL. The groups of mice treated with a PBS phosphate buffer had similar tumour growth kinetics in beige mice and in nude mice. (*) represents significantly larger tumours in groups of mice depleted by NK1.1 compared with animals treated with FL alone. This experiment was reproduced twice with identical results.

Figure 6:
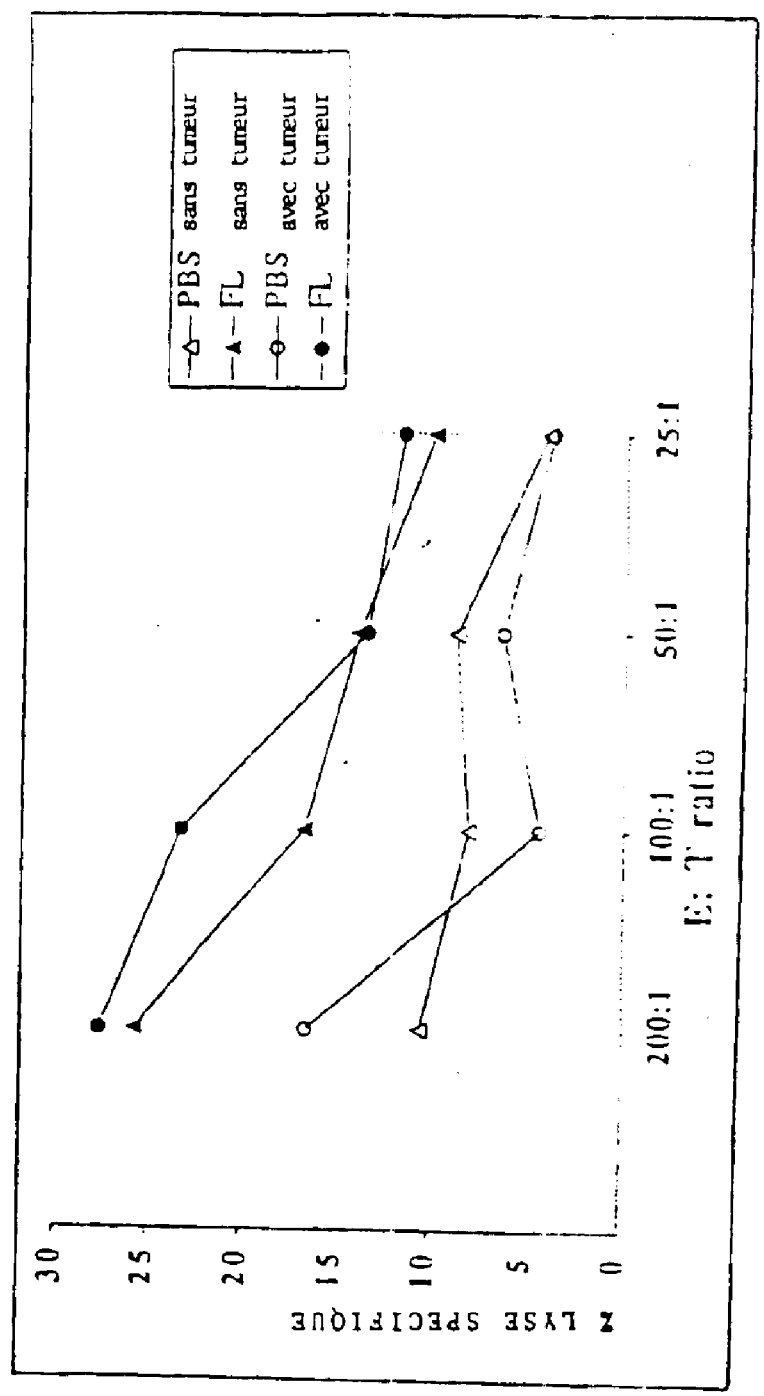

FIG. 6: FL therapy is accompanied by an increased NK activity in the spleen of B6 mice.

Splenocytes of mice without a tumour or with an AK7 tumour were prepared after 20 days treatment in a phosphate buffer (PBS) or FL, and used as effector cells in a chromium release test using YAC-1 cells as target cells. The results are expressed as the specific lysis percentage at different effector.target ratios. Each group comprised 3 mice.

FIG. 7: Role of lymphoid dendritic cells, of B7/CD28 interaction and of cytokines associated with Th1 differentiation in the anti-tumoral NK cell dependent effect induced by FL.

(a) In vivo depletion experiments using anti-CD8α or anti-CD4 antibodies in B6 nude mice. B6 nude mice with tumours were treated with FL alone or associated with anti-CD8α or anti-CD4 antibodies using the protocol described in the Method and Apparatus section. The tumour size was determined twice a week for groups of 5 animals. (*) represents tumours with a significantly smaller size in groups of mice injected with FL and not depleted compared with animals treated with anti-CD8α antibodies. These data were reproduced twice with similar results.

(b) In vivo co-administration of CTLA41g. Similar experiments were carried out with CTLA41g mice as described in the Method and Apparatus section. (*) represents tumours with a significantly larger size in the group of mice injected with CTLA41g compared with animals treated with FL alone. These data were reproduced twice with similar results.

(c) In vivo co-administration of anti-p40-mIL-12 monoclonal antibody. Similar experiments were carried out with the anti-p40-mIL-12 antibody as described in the Method and Apparatus section. No significant blockage of anti-tumoral activity was observed. These data were reproduced twice with similar results.

(d) In vivo co-administration of anti-IFNγ monoclonal antibody. Similar experiments were carried out with an anti-IFNγ antibody. (*) represents tumours with a significantly larger size in groups of mice treated with anti-IFNγ antibody compared with animals treated with FL alone. These data were reproduced twice with similar results.

FIG. 8: Adoptive transfer of dendritic cells from the spleen to B6-nude mice with AK7 tumours: prophylactic and therapeutic anti-tumoral effects. 8a: 2 to 5 million immature dendritic cells were directly injected subcutaneously and intratumorally into B6-nude mice with day 1 AK7 tumours (prophylactic). The injections were carried out twice a week for 15 days. Tumour growth was monitored and compared with a group of animals treated with PBS (five mice per group) using a t-student test. Results with 95% significance are indicated with a (*). 8b: Idem, but the dendritic cells were injected into 20 day established AK7 tumours (therapeutic).

Figure 9A:
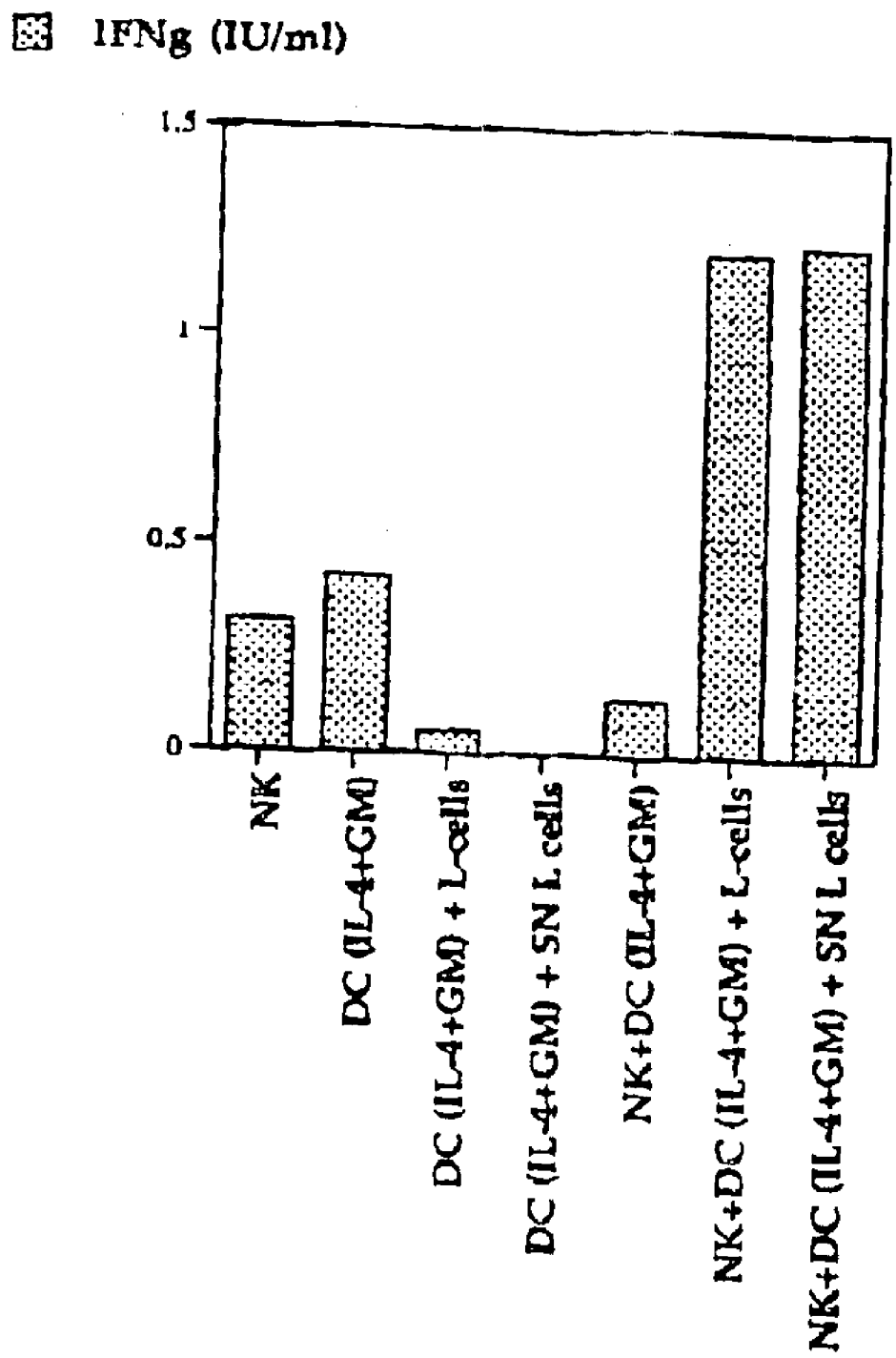
Figure 9B:
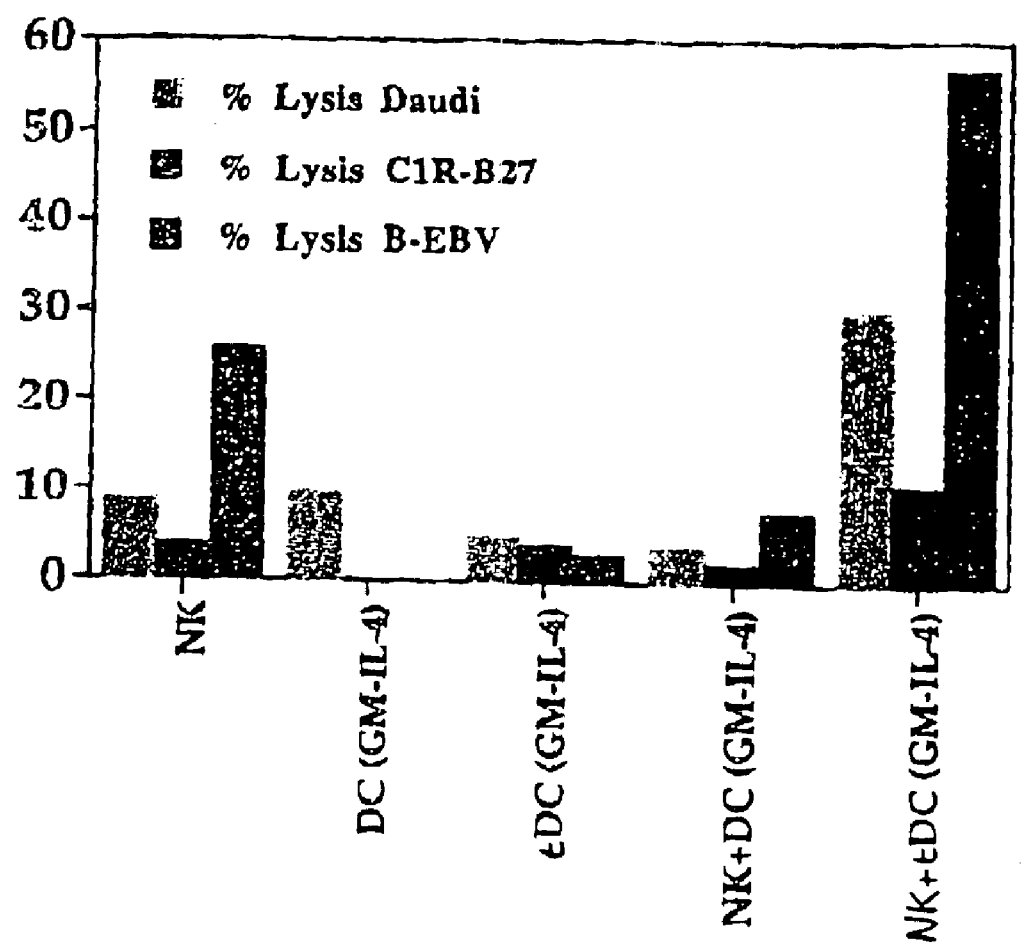

FIG. 9: Activation of human NK cells purified from PBL of healthy or sick donors by immature dendritic cells triggered in the presence of fibroblasts (L-cells) or supernatant (SN L cells). 9a: Measurement of IFNγ secretion. The results are expressed in IU/ml, repeated in at least three separate experiments. 9b: Measurement of cytolysis of tumour targets by released chromium analysis (tDC= triggered dendritic cell).

FIG. 10: Exosomes of murine dendritic cells (DEXm) activate murine NK cells. 10(a): Measurement of interferon gamma protection; 10(b): Measurement of YAC1 cell cytolysis; 10(c): Measurement of NK cell survival rate; 10(d): Measurement of average tumour size in vivo. Dex BM-DC: dexosomes produced from dendritic cells derived from bone marrow. E:T ratio: ratio of effector cells to target cells. SN BM-DC: direct supernatant of dendritic cells derived from bone marrow.

Figure 11:
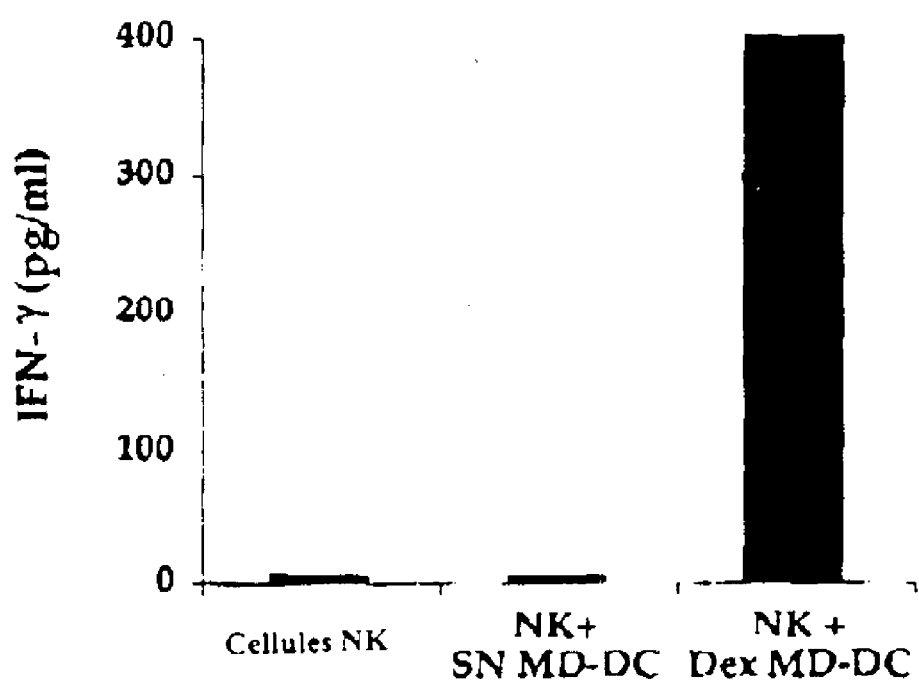

FIG. 11: Human dendritic cell exosomes (DEXh) activate resting murine NK cells. Dex MD-DC: dexosomes produced from dendritic cells derived from monocytes. SN MD-DC: direct supernatant from dendritic cells derived from monocytes.

FIG. 12: Dendritic cell exosomes (DEXm) from "Knock-Out" mice for the $\beta_2$-microglobulin gene (12a) or for class II MHC molecules (12b) activate murine NK cells. B6wt: wild type B6 mouse; β2m-/-: "Knock-Out" mouse for the $\beta_2$-microglobulin gene: Ci II-/-; "Knock-Out" mouse for class II MHC molecules.

FIG. 13: Relative activities of dendritic cells and the dexosomes which they produce to stimulate NK cells. 13(a) Comparative study of dendritic cell activity produced in low doses or in high doses of interleukin-4, and the dexosomes they produce. 13(b) Comparative study of activity of triggered or non triggered dendritic cells, and the dexosomes they produce.

METHOD AND APPARATUS

1. Animals

Female C57-BL/6 (B6) and BALB/c scid/scid (SCID) mice were obtained from the Centre d'Elevage Janvier (Le Genest St-Isle, France). Female C57/BL/6-bg/bg (B6-beige) mice were purchased from Harlan UK Limited (Oxfordshire, England). Female C57-BL/6-B6-nude (B6-nude) mice were obtained from the Mollegaard Research and Breeding Centre (Skensved, Denmark). Male and female C57BL/6 Rag2-/- (B6-Rag-/-) were purchased from the Centre de Développement des Techniques Avancées at the Centre Nationale de la Recherche Scientifique (Orléans, France). The SCID beige and B6-nude mice were kept under non pathogen conditions. The mice were grouped by age (8 to 10 weeks) at the start of each experiment.

2. Cell Cultures

AK7 cells, provided by A. Kane (Brown University, Providence, R.I.), are a murine mesothelioma line generated by intra-peritoneal injection of crocidolite asbestos fibres into B6 mice. This cell line was maintained in DMEM medium supplemented with 10% foetal calf serum inactivated by heat treatment, 1.0 mM of sodium pyruvate, 2 mM of L-glutamine, 100 IU/ml of penicillin, and 100 µg/ml of streptomycin. The tumoral cell lines were maintained in vitro, for a period not exceeding one month before the in vivo experiments. The murine dendritic cell lines were maintained in an IMDM medium containing 10% of inactivated foetal calf serum, 2 mM of L-glutamine, 50 µM of 2-βME, 100 IU/ml of penicillin, and 100 µg/ml of streptomycin (IMDM medium). In order to cause the cells to mature, recombinant mouse TNF-α (R&D Systems, Abingdon, UK) was added in a concentration of 10 ng/ml for 24 hours. Maturation could also be induced by incubating cells in the presence of LPS (1–10 µg/ml). The YAC-1 cell line is a lymphoma line in an A/Sn context which is highly sensitive to NK cells. P815 cells are mastocytoma cells in a DBA/2 context which are resistant to NK cells. All of the culture media and reactants were obtained from GIBCO BRL (Life Technologies, Merelbeke, Belgium).

3. Generation and Culture of Dendritic Cells Derived from Bone Marrow

The murine dendritic cells originated from differentiation of precursor cells of bone marrow cultivated in the presence of GM-CSF and IL-4 for 6 days in a RPMI 1640 medium supplemented with 10% foetal calf serum, L-glutamine, essential amino acids, penicillin, streptomycin and β-2ME. These cells were obtained using a protocol described by Mayordomo et al. (1996). Briefly, bone marrow was extracted from tibias and femurs, depleted in lymphocytes and macrophages, and plated onto 24 well culture plates ($0.25 \times 10^6$ cells/ml) in the RPMI 1640 medium defined above supplemented with rm IL-4 and rm GM-CSF (100 IU/ml in each). On day 3, non or slightly adherent cells were harvested and plated onto 24-well culture plates ($0.3 \times 10^6$ cells/ml) for 3 additional days of culture with the same, fresh medium. The dendritic cells obtained had the expected phenotype. The dendritic cells obtained were immature cells. They could be caused to mature in a culture combining interleukin-4 and GM-CSF with TNF-α (10 ng/ml) and/or LPS (1–10 µg/ml). The cells were used for co-culture 24/48 hours after the maturation stimulus. Autologous or allogenic dendritic cells were used for co-culture with the same efficiency. Further, mature and immature dendritic cells could be used to equal effect.

4. Triggering of Dendritic Cells

The dendritic cells could be triggered using different protocols. One method used in the examples comprised co-culturing dendritic cells (mature or immature) in the presence of dividing fibroblast cells (in particular cells from the L-929 or NIH 3T3 line). Co-culture was generally maintained for 24–48 hours; tDC could be obtained from about 20 hours of co-culture. In a further method, dendritic cells were incubated in a triggering medium, advantageously comprising a culture supernatant of dividing fibroblast cells (in particular cells from the L-929, NIH3T3 or MRC5 line, primary culture of human pulmonary fibroblasts). In the following examples, the supernatant used was diluted to a third, and the cultures were made in a medium comprising IL-4 and GM-CSF. A further triggering experiment was carried out using a medium comprising a tumoral cell supernatant (mastocytoma) as the triggering medium.

5. Generation of NK Cells

Resting NK cells were obtained from the spleens of SCID or Rag2 -/- mice after a plastic adhesion step for 2 to 3 hours at 37° C. Briefly, the spleens of B6-Rag-/- or SCID mice were dissociated in complete RPMI 1640 medium as defined above to generate cell cultures in suspension. After lysing the erythrocytes, the cells were washed once and plated ($2.5 \times 10^6$ cells/ml) for 2 to 3 hours at 37° C. Non-adherent cells were harvested and counted. These cells were essentially composed of resting NK cells.

6. NK/DC Co-culture

For co-culture, immature or mature, autologous or allogenic, triggered or non triggered dendritic cells were harvested, washed three times and added in different concentration ratios to resting NK cells, freshly isolated ($1 \times 10^6$ NK cells/ml) in U-bottomed 96 well plates. The individually incubated cells (dendritic cells or NK cells) were plated in similar concentrations as controls.

7. Interferon γ Secretion Test

Supernatants from dendritic cell/NK cell co-cultures were collected and if necessary frozen at −70° C. Tests for interferon γ release were carried out using commercially available ELISA kits (Genzyme Corp, Cambridge, United States). The limit of detection for the tests used was close to 5 pg/ml. The effects of doses were tested by varying the ratio of dendritic cells to NK cells.

8. NK Cell Cytotoxicity Test

The in vitro cytotoxicity of NK cells was evaluated using conventional chromium 51 release from NK sensitive (YAC-1) marked or NK resistant (P815) marked targets.

More precisely, cells from NK/DC co-cultures or separate cultures incubated for 40 to 72 hours were collected, marked with Trypan Blue to exclude lymphocytes and dendritic cells, and counted and used as effector cells in a cytotoxicity test using YAC-1 and P815 cells as target cells. The target cells were pre-incubated for 1 to 2 hours at 37° with $Na^{51}CrO_4$ (100 $\mu Ci/10^6$ cells; New England Nuclear), washed once, and incubated in RPMI 1640 medium supplemented with 5% inactivated foetal calf serum, for ½ an hour at 37° C. The cells were then washed 3 times and plated at $2\times10^3$ cells per well on V bottom 96 well microtitration plates. The effector cells and targets were mixed in different effector/target ratios in a total volume of 0.2 ml and incubated for 4 hours at 37° C. The degree of lysis of target cells was measured by counting 0.1 ml of supernatant transferred to a Luma plate. Spontaneous release was determined from wells containing marked target cells alone and the maximum chromium 51 release was determined by adding 2% cetrimide. The specific cytotoxicity was calculated as follows: percentage of release of chromium$^{51}$=100×(experimental count cpm)–spontaneous release count cpm)/(maximum release count cpm=spontaneous release count cpm).

For the in vivo tests, the spleens of 2 or 3 mice with AK7 cells of free of tumours were removed after 20 days treatment with FL or with a phosphate buffer (PBS). Suspensions of splenocyte cells depleted in erythrocytes by osmotic lysis were used immediately as effector cells in a cytotoxicity test using YAC-1 cells and P815 cells as targets, as described above.

9. In Vivo Treatment of Mice by FL

Mice were inoculated intradermally into the right flank with the minimum tumorigenic dose of AK7 cells ($3\times10^9$ cells) in a 0.1 ml volume of PBS. The FL compound derived from CHO cells was supplied by Immunex Corp (Seattle, USA, Lynch et al., Nature Medicine 3: 625: 1997). This cytokine was used diluted in PBS to 100 $\mu g$ per ml. Established 20 day AK7 tumours (about 20 mm$^2$ in diameter) were treated by a single daily injection (subcutaneously into the left flank) of either FL or PBS (10 $\mu g$) in a total volume of 0.1 ml for 20 consecutive days. Tumour growth in the mice was monitored twice a week and the average tumour size was illustrated by measuring two perpendicular diameters in millimeters using callipers. The rates of tumour growth were determined by recording the tumour size (mm$^2$) over time after day 1 of FL treatment. All of the studies were carried out at least 4 times with groups of 5 animals.

10. In Vivo Antibody Depletion Experiments

Anti-CD8α antibodies (rat clone YTS 191.1.2, IgG2a), anti-CD4 (rat clone YTS 169.4.2.1, IgG2a) and anti-NK1.1 antibiotics (mouse clone PK136, IgG2) were used in the depletion experiments. The hybridomas were cultivated in athymic mice and the ascitic fluids were harvested and purified using the techniques described above by precipitation with caprylic acid then ammonium sulphate, dialysis against PBS, then adjustment to 1 mg/ml (McKinney, 1987). Unless otherwise indicated in the key to the figures, depletion was commenced on day 1 of FL treatment of B6 mice, 200 to 300 $\mu g$ of monoclonal antibody was injected intra-peritoneally for 3 consecutive days, then every other day during the FL treatment. After FL treatment, the monoclonal antibodies were administered twice at 4 day intervals. Experiments carried out in parallel by flux cytometry using fluorescent antibody confirmed that the depletion observed were over 99% for targeted cellular sub-populations, on day 9 and day 20 of the FL treatment. For the B7 blocking experiments, the mice were injected intra-peritoneally with 200 $\mu g$ of CTLA41g mouse fusion protein (supplied by L. Adorini, Hoffman La Roche, Italy) at 2 day intervals between day 10 and say 18 of the FL treatment. For the endogenous IL-12 neutralisation studies, purified anti-p40 IL-12 antibody (rat clone C-17-8, IgG2a) was injected intra-peritoneally at individual doses of 300 $\mu g$ at 3 day intervals between day 5 and day 17 of the FL treatment. For the endogenous interferon γ neutralisation studies, 300 $\mu g$ per mouse of anti-interferon γ antibody (hamster IgG) was injected intra-peritoneally on days 10, 15 and 20 of the FL administration. All of the experiments were carried out with 5 mice per group and at least twice.

11. Adoptive Transfer of Dendritic Cells in Mice

B6-nude or SCID mice with a 1 day or 20 day AK7 tumour were injected intra-tumorally and subcutaneously twice a week with 2 to $5\times10^6$ immature dendritic cells, for two weeks. Five mice per group were treated. Tumour growth was monitored as described above.

12. Statistical Analysis of Data

The exact Fisher method was used to interpret the significance of the differences between the different experimental groups (shown as an average with a standard deviation). To interpret the passive dendritic cell transfer experiments, 2 groups were compared using the Student t-test. The 95% significance of the results is shown for each individual experiment.

EXAMPLES

The results shown in the following examples demonstrate, in particular:

1) that co-culture of dendritic cells and purified NK cells entrains survival of mature dendritic cells and NK cells and rapid activation of NK cells; in other words, the dendritic cell, in contrast to any other known cell, can render a NK cell an effective killer and secretor of IFNγ against natural NK-sensitive targets, without the addition of cytokines and without showing detectable levels of IL-2, IL-12 secretion in these co-cultures;
2) that adoptive transfer of dendritic cells or direct in vivo expansion of dendritic cells causes large anti-tumoral effects due to NK activation.

Example 1

Dendritic CellsStimulate Cytolytic Activity and the Production of Interferon γ by NK Cells In Vitro This example illustrates the properties of dendritic cells at different stages of differentiation to activate resting NK cells in vitro. Cytotoxic activity, interferon γ production and proliferation were tested.

In a series of experiments, dendritic cells freshly derived from syngenic bone marrow were cultivated in the presence of interleukin-4 and GM-CSF and kept in an immature state (see Method and Apparatus section). The immature dendritic cells were collected, washed intensively and co-incubated in an initial ratio of about 1:1 with non-adherent mononuclear cells obtained from splenocytes freshly harvested from syngenic SCID BALB/c mice in a complete medium in the absence of cytokine. A third of these non-adherent splenocytes were positively marked with Dx5 monoclonal antibody or with monoclonal anti-NK1.1 antibody. After co-culture for 40 to 72 hours, the NK cells were counted and tested in a cytotoxicity test by measuring chromium 51 release over 4 hours against YAC-1 cells and P815 cells in different effector/target ratios.

The results obtained are shown in FIG. 1 and demonstrate that these dendritic cells induced activation of cytolytic activity of NK cells. In particular, these results show:

that co-culture of the two cell types enabled viable NK cells to be recovered; and that when NK cells and dendritic cells were co-incubated in a ratio of 0.1 to 0.3:1, 20% to 50% specific lysis of YAC-1 cells was obtained in an effector cell/target cell ratio of 25 to 100:1. P815 cells, which are NK insensitive, were not lysed under the test conditions and none of the two cell populations (NK cells and dendritic cells) cultivated separately in similar concentrations induced any significant YAC-1 cell lysis (FIG. 2).

Figure 2A:
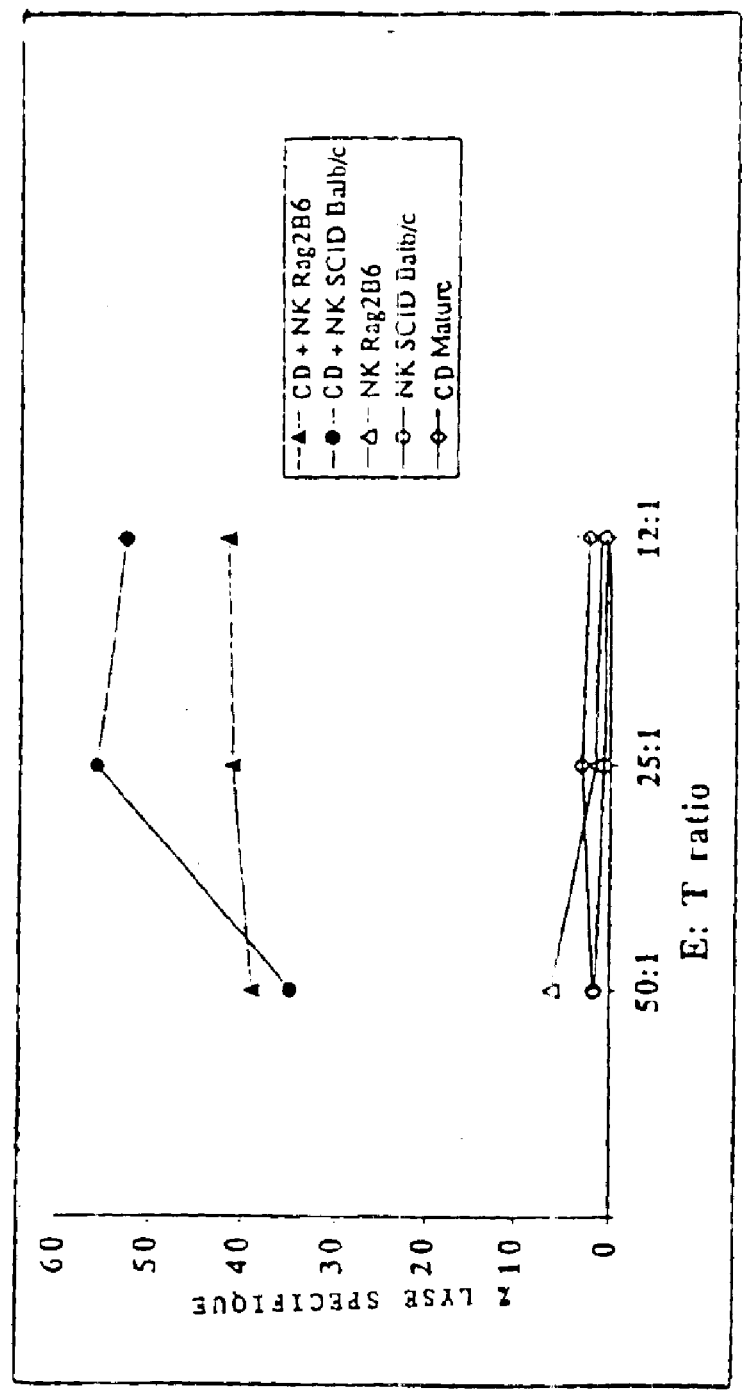

A further series of experiments used a spleen dendritic cell line. This line was maintained under culture conditions enabling long term growth of cells in their immature stage and their triggering. This line was then induced to mature in the presence of TNFα or LPS for 24 hours. The matured cells exhibited large morphological changes as previously described by Winzler et al. The aggregates were no longer adherent and FACS showed high expression of CD11c, I-Ab, B7.2 and CD40 molecules. These mature dendritic cells were tested under the same conditions as those described above, by co-incubation for 40 to 48 hours with resting NK cells freshly collected from B6-Rag-/- mice in different ratios. The results obtained are shown in FIG. 2. These results show that:

co-culture of two cell types enabled significantly more viable NK cells to be harvested from the wells than from a separate culture of NK cells (10% to 30% vs 2% to 5%);

when NK cells and dendritic cells were co-incubated in a ratio of 0.1 to 0.3:1, a specific lysis of 40% to 60% of YAC-1 cells was obtained in a target cell/effector cell ratio of 25:1. P815 cells, which are NK insensitive, were not lysed under any of the test conditions. None of the two cell populations (NK cells and dendritic cells) cultivated separately in culture medium at similar concentrations induced any significant lysis of YAC-1 cells (FIG. 2a). Lysis of other slightly positive class I MHC tumour cells, such as MCA205, MCA101, TS/A or AK7, was also observed in the presence of activated NK cells (results not shown).

The results obtained also shown that the supernatant from NK-DC co-culture contained significant levels of interferon γ which reduced as a function of the number of stimulating dendritic cells (FIG. 2b). in contrast, interferon γ was not detectable in the supernatant from the separately cultivated dendritic cells or NK cells. No significant proliferation was observed under these co-culture conditions as determined by thymidine incorporation after co-culture for 40 to 70 hours.

These results thus show the capacity of immature and mature dendritic cells to stimulate the activity of NK cells both for interferon γ production and for the specific lysis activity against tumour cells, sometimes in excess of the KIR effect.

Figure 2B:
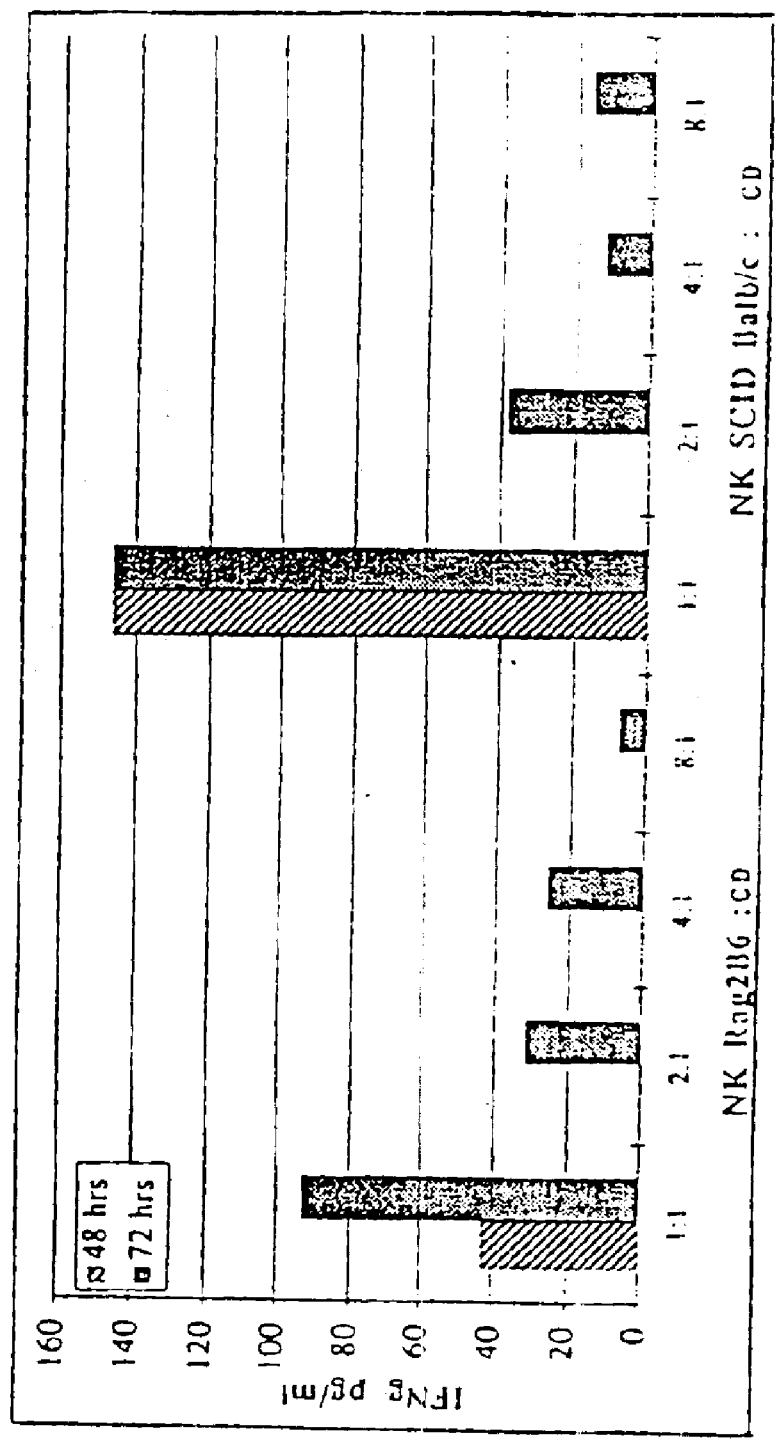

In similar manner to the above experiments, it was also demonstrated that allogenic dendritic cells were capable of stimulating NK cell activation. Briefly, non-adherent allogenic SCID BALB/c mouse splenocytes were activated by co-culture for 40 to 48 hours in the presence of mature dendritic cells in a NK:DC ratio of 0.1 to 0.3:1. The results are shown in FIGS. 2a and 2b and show that these allogenic dendritic cells activated both the lytic properties of NK cells and the production of interferon γ.

These results clearly show that mature or immature, autologous or allogenic dendritic cells, whether derived from bone marrow or from the spleen or from established dendritic cells lines, are capable, when triggered, of efficiently activating the lytic activity of NK cells and interferon γ production by NK cells.

Example 2

Stimulation of NK Cells by Dendritic Cells Involves Direct Cell Contact

Mature dendritic cells are known to secrete different cytokines such as IL-12, IL-15, IFNα/β or TNFα which could be responsible for activation of NK cells. A transwell culture system was used to determine the possible involvement of soluble factors in the activation of NK cells by dendritic cells. The results shown in FIG. 3 demonstrate that cytolytic activity and production of interferon γ by NK cells in response to dendritic cells is only detected in the case where NK cells are co-incubated in contact with dendritic cells but not when the cells are separated by a porous membrane. These results thus show that activation of NK cells by dendritic cells requires contact or a direct cell/cell interaction, and that this activation involves a co-stimulation factor, present in the membrane of dendritic cells.

Example 3

Expansion of White Blood Cells of the Dendritic Line by FL is Accompanied by Regression of an Established Negative Class 1 Tumour in B6-Nude or in Rag2 B6-/- Mice AK7 cells represent a slightly immunogenic syngenic B6 mouse mesothelioma line which spontaneously infiltrate the peritoneal cavity after prolonged establishment in the abdominal wall. The AK7 tumour obtained expresses very low levels of class 1 molecules in vitro. Treatment of 20 day established AK7 tumours in B6-nude mice with FL induced a transient suppression of tumoral growth and finally a significant slowing in the growth in vivo (see FIG. 4). In contrast, FL exerted no direct cytotoxic effect on AK7 cells in vitro. These anti-tumoral effects in vivo start to be observed on day 10 of treatment with FL when a splenomegaly and adenomegaly, attributable to expansion of white blood cells of the dendritic line, were observed.

The tumour growth kinetics regained a normal rhythm 5 to 10 days after FL treatment was stopped, when the number of dendritic cells decreased. The anti-tumoral effects induced by FL observed in B6-nude mice or Rag2 B6-/- mice were also as pronounced as those for immunocompetent mice (FIG. 5b), emphasising that neither T cells nor B cells are involved in slowing tumour growth.

These results thus demonstrate that administration of a dendritic cell growth factor induces regression of negative class 1 tumours. These results also show that this effect is not due to the activity of T or B cells.

Example 4

Antitumoral Effects Mediated by FL are not Observed in the Beige Mouse and are Blocked by Administration of a Monoclonal Anti-NK1.1 Antibody in Immunocompetent Mice with a Tumour In order to determine the mechanisms of the anti-tumoral effects induced by FL more precisely, B6-beige mice with an AK7 tumour were treated with FL using a similar therapeutic regime.

Figure 5A:
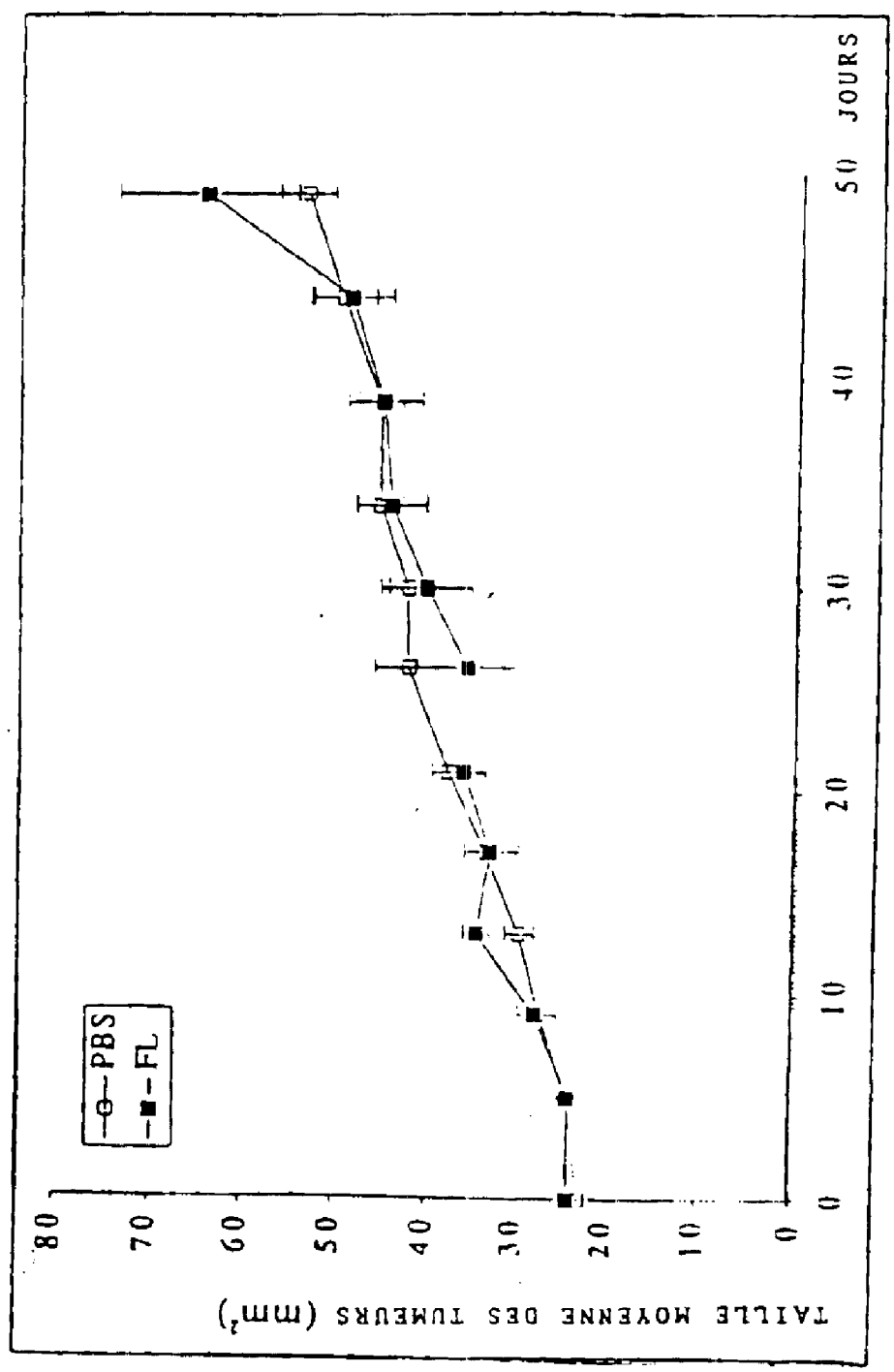
Figure 5B:
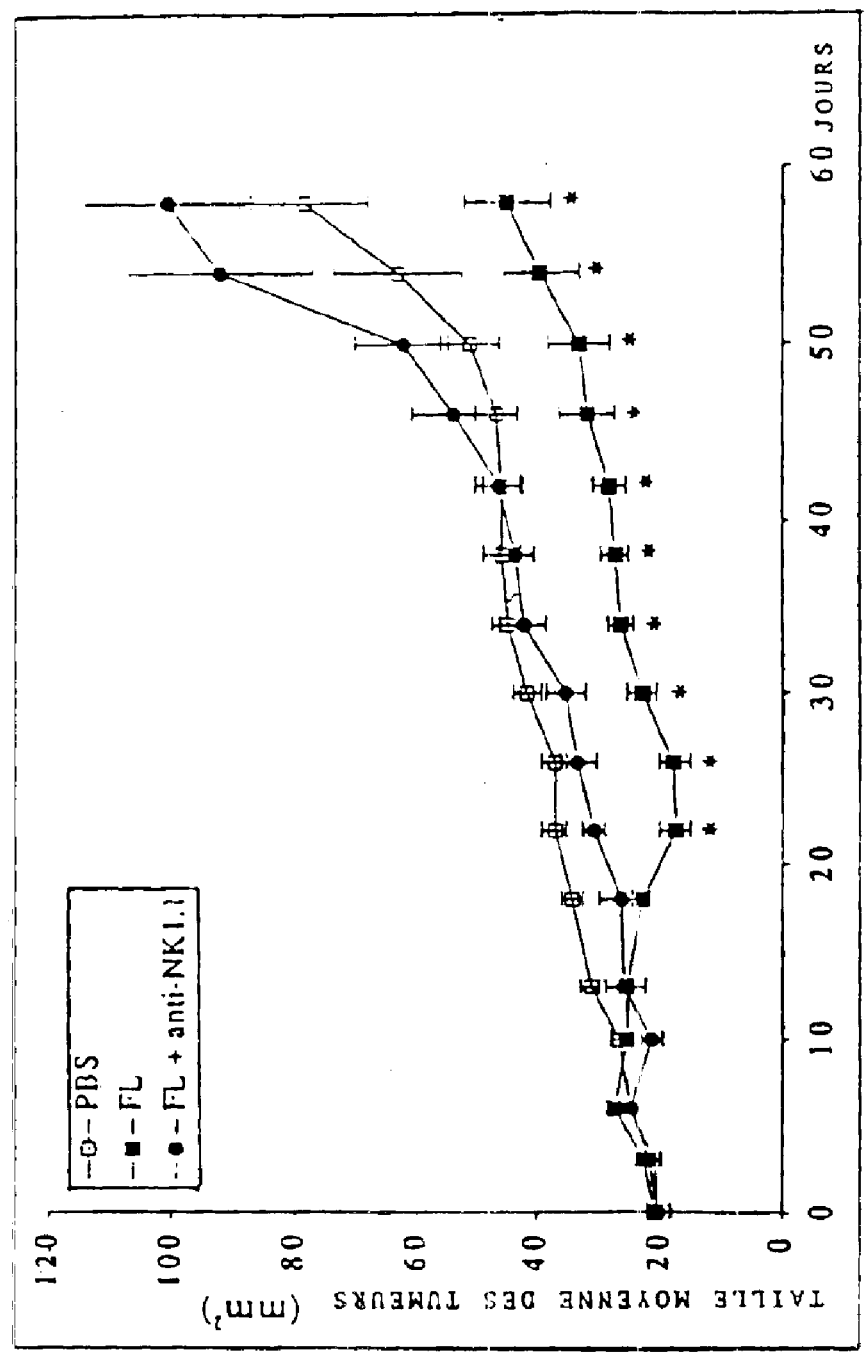

The B6-beige mice had mesotheliomas which slowly grew until they caused death despite administration of FL (FIG. 5a). In order to determine the involvement of NK cells in the tumoricidal activity induced by FL more precisely, immunocompetent B6 mice were depleted using monoclonal anti-NK1.1 antibodies. The results shown in FIG. 5b show that this depletion was necessary and sufficient to completely annul the anti-tumoral effects induced by FL. As a result, these results show that NK cells play a necessary and sufficient critical role in the efficacy of FL as an anti-tumoral agent.

Example 5

Compound FL Significantly Increases Splenic NK Activity In Vivo

This example illustrates the capacity of FL to increase the activity of NK cells in vivo. The absolute number of NK cells positively marked with anti-NK1.1 monoclonal antibodies by FACS analysis in splenocytes and mononuclear cells from lymphatic ganglia was slightly increased by 3 to 5 times in mice with tumours and in mice without a tumour. Splenocytes harvested on day 20 from B6 mice treated with FL or with a saline solution, in mice with or without AK7 tumours, were tested for spontaneous cytolytic activity against YAC-1 cells in vitro in a chromium 51 release test over a period of 4 hours. A significant increase in NK activity but not in the production of interferon $\gamma$ was demonstrated in different experiments carried out both with nude or immunocompetent mice, with no significant effect attributable to the presence of the tumour itself (FIG. 6). No lysis was observed against P815 cells. Further, the cytokine levels for interferon $\gamma$ and TNF$\alpha$ in the serum or culture supernatants from mononuclear lymphatic ganglion cells from the spleen were not statistically different under all of the test conditions and no detectable level was observed for IL-1$\beta$ and IL-12. These results show that treatment with FL was associated with an increase in the NK activity in the spleen in vivo.

Example 6

Figure 7A:
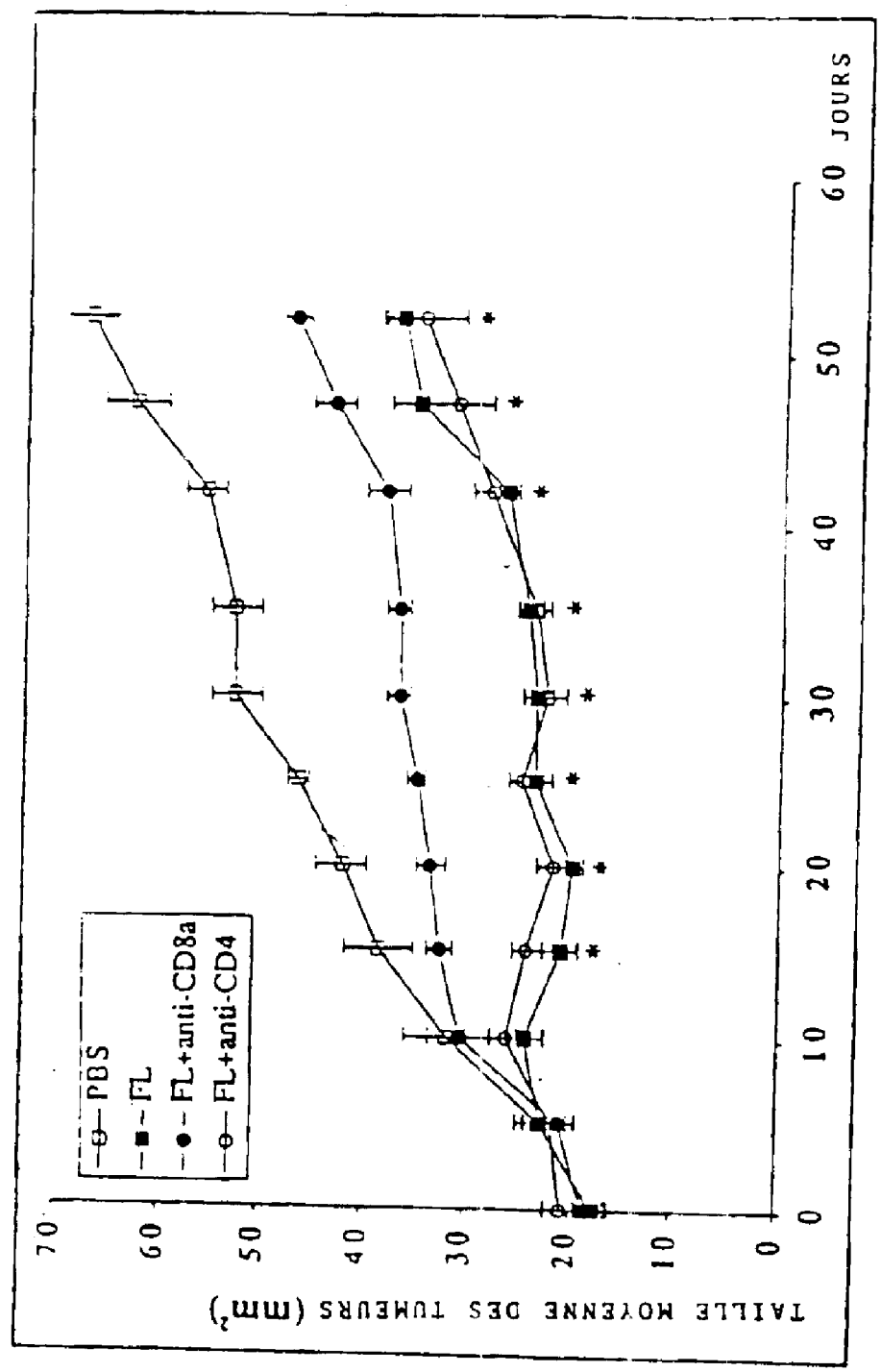

Depletion of Nude Mice by Administration of Monoclonal Anti-CD8$\alpha$ or CTLA4-Ig Antibody Significantly Blocks NK Cell-dependent Anti-Tumoral Effects This example describes the role of sub-populations of myeloid or lymphoid dendritic cells induced by FL in the peripheral increase of cytolytic NK activity and in NK-dependent anti-tumoral effects. Since lymphoid dendritic cells have been described as secreting IL-12 in response to a SAC+IFN$\gamma$ stimulation in vitro and since IL-12 is a NK cell stimulation factor, selective depletion of positive CD8$\alpha$ lymphoid dendritic cells (DEC205+) using a monoclonal anti-CD8$\alpha$ antibody was undertaken in B6-nude mice. The depleting monoclonal antibody was injected as soon as differentiated dendritic cells appeared in the presence of FL (day 0 FL) and was continued up to 10 days after FL treatment in high doses had been stopped. The CD8$\alpha$ molecule was not expressed on the mouse NK cells in the B6-nude mouse, which thus targeted the depletion towards sub-populations of lymphoid dendritic cells. Mice with AK7 tumours depleted with monoclonal anti-CD8$\alpha$ antibody responded significantly less to FL treatment than non depleted control mice or mice injected with anti-CD4 antibody (FIG. 7a). However, FL remained effective in mice which had received FL and were depleted for positive CD8$\alpha$ cells, when compared with animals not treated with FL, emphasising that lymphoid dendritic cells are only partially involved in the NK cell-dependent anti-tumoral effects. The small population of myeloid dendritic cells expressing the CD4 marker do not appear to participate in these anti-tumoral effects (FIG. 7a).

Figure 7B:
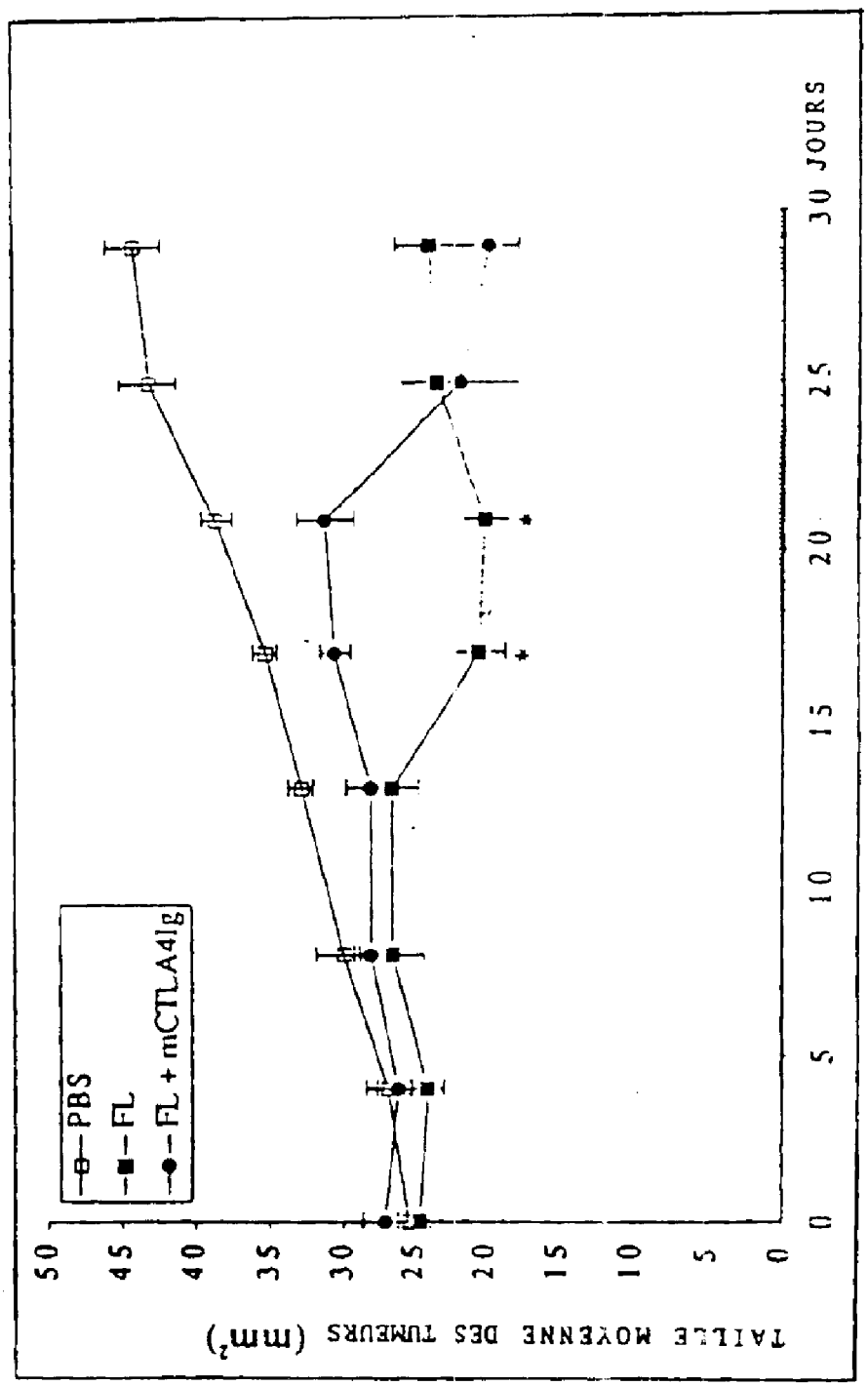

To further confirm the critical role of dendritic cells in the NK-dependent anti-tumoral effects, B7 co-stimulation molecules, which are known to be involved in the effector phase of recognition by NK cells, were targeted using a systemic injection of CTLA4-Ig murine fusion protein. During the complete period of CTLA4-Ig administration, a statistically significant loss of FL efficacy on the suppression of tumoral growth was observed (FIG. 7b). In contrast, injection of human IgG in the control experiment did not alter the efficacy of FL in vivo. It should be emphasised that the AK7 tumour does not express B7 molecules in vitro. Taken as a whole, these data show that positive B7 cells and/or dendritic cells are essential for the NK cell-dependent anti-tumoral effects obtained by the growth factor FL.

Example 7

Interleukin 12 is not Involved in Anti-tumoral Effects Induced by FL

Figure 7C:
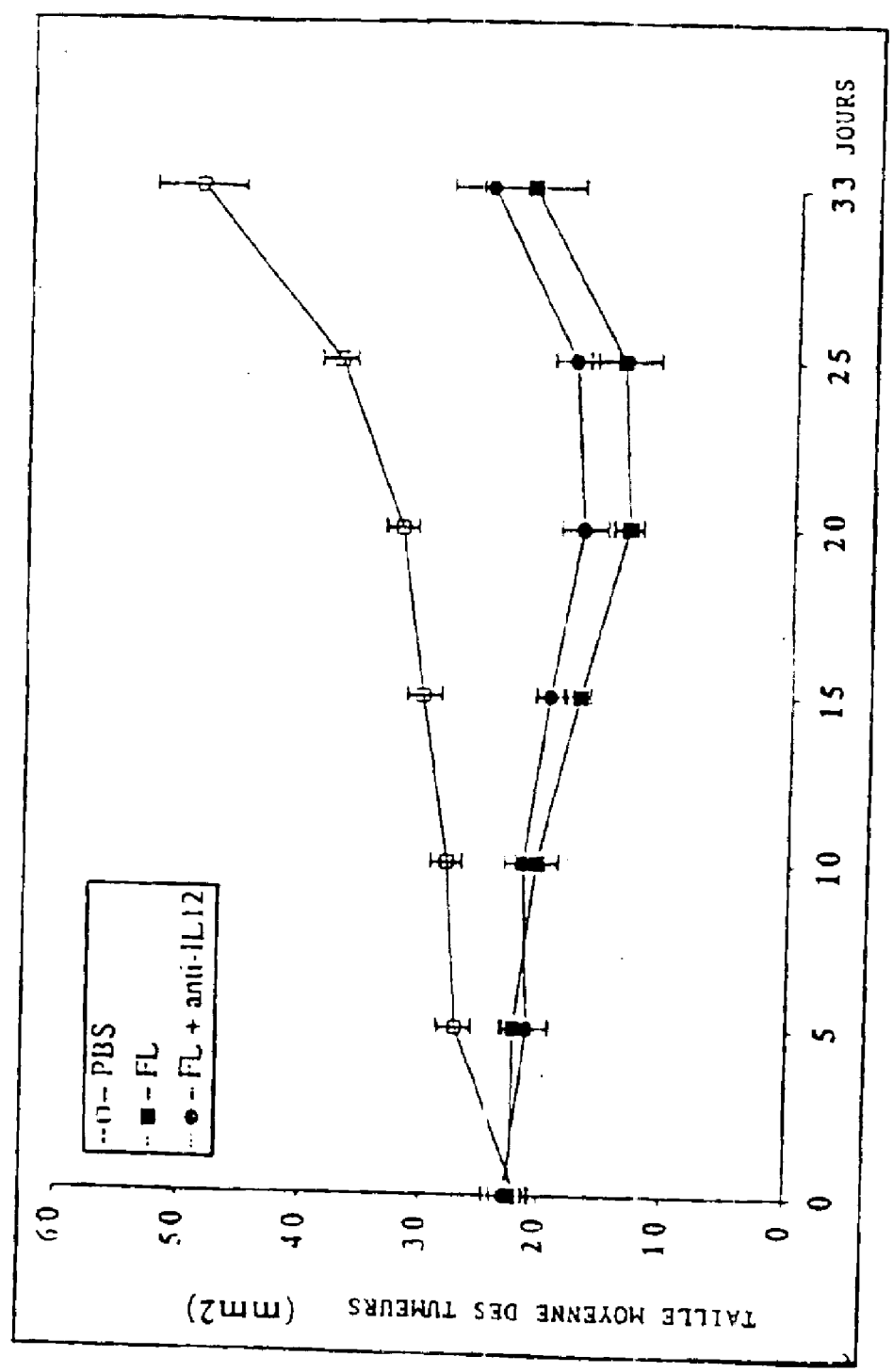
Figure 7D:
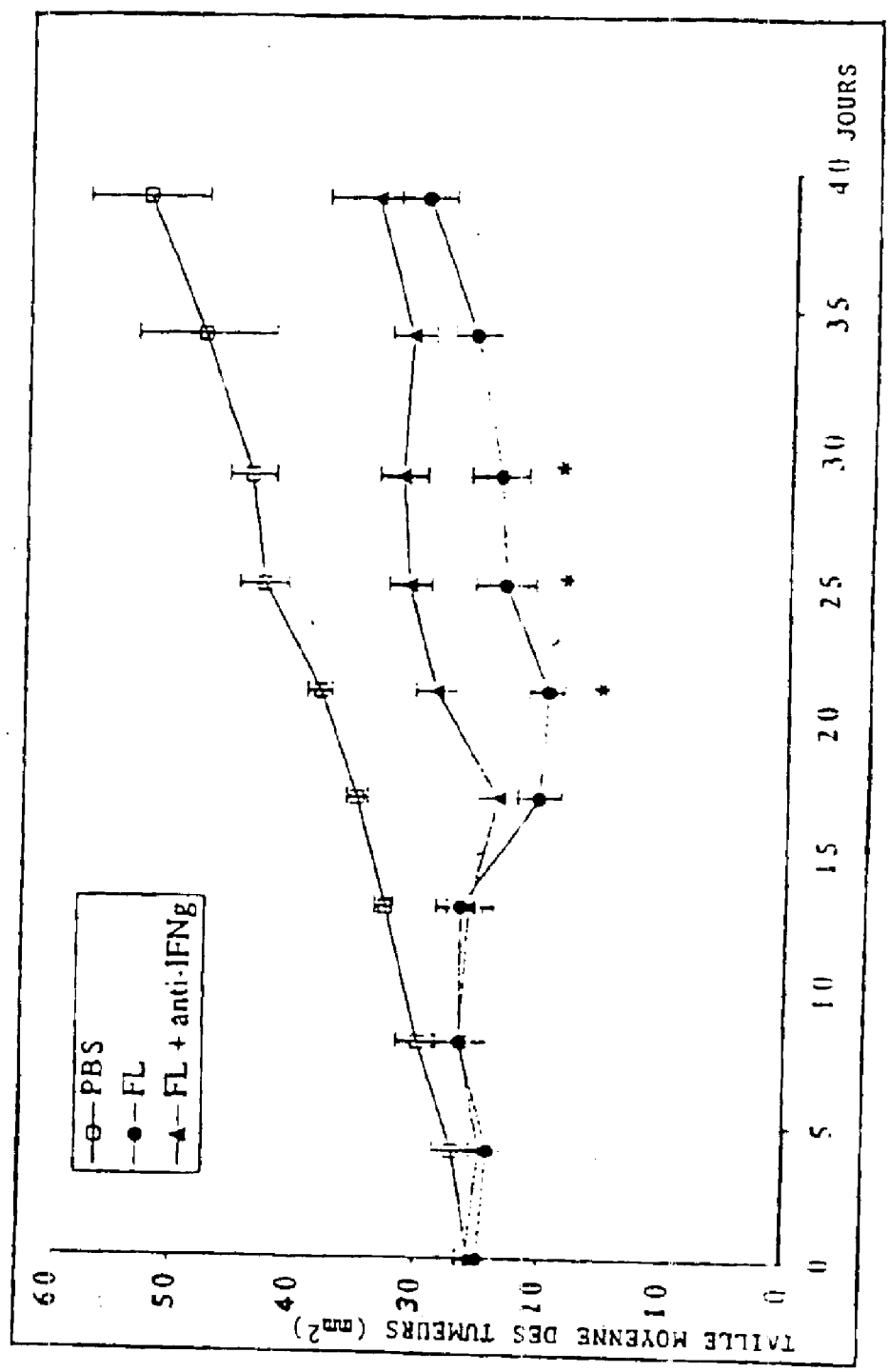

IL-12 and IFN$\gamma$ cytokines are type Th1 T cytokines which are known to stimulate NK activity in vivo. Further, as described in the preceding example, the lymphoid dendritic cell sub-population capable of secreting IL-12 is important for the observed anti-tumoral effect. Although the levels of IL-12 in the serums or supernatants from lymphatic ganglia or spleens derived from mononuclear cells were undetectable in animals treated with FL, mice were injected with neutralising anti-p40 IL-12 antibody from day 5 until day 20 of FL treatment. No inhibiting effect of these monoclonal antibodies on the anti-tumoral effects induced by FL was observed in vivo (FIG. 7c). Neutralisation of interferon $\gamma$ in vivo, in contrast, temporarily blocked the anti-tumoral effects mediated by FL which implies that NK cytotoxicity is mediated by IFN$\gamma$ since the mesothelioma is IFN$\gamma$ sensitive (FIG. 7d). Other results obtained confirm these observations. In particular, (i) knock-out mice for the type-1 interferon receptor always had NK cells which could be activated by dendritic cells in accordance with the invention, (ii) the supernatants from these co-cultures did not cause CTLL2 to proliferate, which attests to the absence of IL-2 or IL-15 produced under these conditions, and (iii) the anti-IFN$\gamma$ antibody interfered only slightly with the in vivo activity of FL.

Example 8

Adoptive Transfer of Dendritic Cells at the Start of Tumour Establishment or During Tumour Growth at Day 20 in SCID Mice Affects Tumour Growth In order to positively remove any indirect event which could account for the increase in NK activity independent of the developed population of dendritic cells and to formally test a direct in vivo dialogue effect between dendritic cells and NK cells, 2 to 5 million immature dendritic cells were passively transferred by subcutaneous injection twice a week for two weeks from AK7 day 1 or from day 20 into B6-nude mice or SCID mice with AK7 tumours, which are known to have a high NK activity.

Figure 8B:
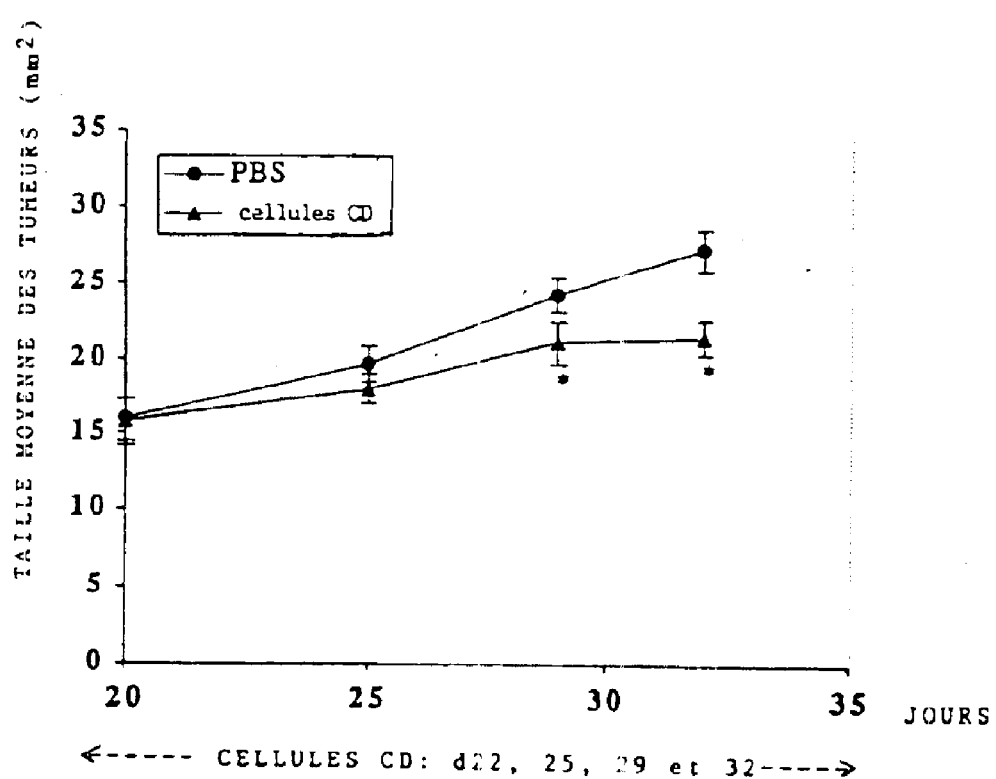

The results are shown in FIGS. 8a and 8b and show a significant slowing of tumour growth in the group of mice treated with dendritic cells compared with the control group. These results clearly demonstrate the role of dendritic cells in stimulating the activity of NK cells in vivo.

Example 9

Triggering Immature Dendritic Cells Using a Xenogenic Triggering Medium

This example illustrates the fact that immature dendritic cells can be triggered in a xenogenic medium (in the presence of a factor), and that triggering does not modify their maturity state.

$5 \times 10^6$ immature DC derived from monocytes (MD-DC), in IL-4+GM-CSF (CM) for 8 days, were cultivated for 24–48 hours (from day 8 to day 10) in the presence:

either of a medium composed of CM (⅔ of final medium) and a triggering medium (⅓ of final medium) corresponding to the supernatant of $10 \times 10^4$ L-929 fibroblasts cultivated for 48 hours;

or in a CM medium, in the presence of $1 \times 10^6$ irradiated L-929 fibroblasts (5000 rads).

After 48 hours of incubation, the MD-DC were recovered and co-cultured alone or in the presence of allogenic human NK cells, purified by negative immunoselection from healthy donor blood (culture ratio: 2 DC per 1 NK, NK concentration $0.3 \times 10^6$/ml). The DC/NK co-culture or DC alone or NK alone supernatant was then evaluated using ELISA to analyse the IFNγ. In parallel, the co-culture cells were recovered, counted and placed on 51Cr chromium targets to evaluate their lytic power for 4 hours. The results obtained are shown in FIG. 9. These results clearly show the high capacity of triggered immature dendritic cells to activate IFNγ secretion and the lytic activity of resting NK cells.

Example 10

Activation of NK cells by a Preparation Derived from Dendritic Cells

This example illustrates the fact that preparations derived from dendritic cells can be used to activate NK cells. In particular, this example shows that membranous vesicles (or dexosomes) produced from dendritic cells activate NK cells.

In this example, human MD-DC cells were cultivated from the adherent fraction of monocytes from healthy subjects or subjects with metastatic tumours (melanomas, myelomas, lymphomas) in a AIMV+PeniStrepto+L-Glutamine+10% FCS+1000 IU/ml of IL-4 and GM-CSF type culture medium. The medium was changed on day 5 or 6 then the supernatants of these MD-DC, incubated at 37° C., 5% $CO_2$ for 24–48 hours, were passed through a 0.2 μm filter then ultracentrifuged at 70000 g to isolate the dexosomes.

Murine BM-DC were cultivated and triggered as described in the Method and Apparatus section (points 3 and 4). Further, medullar precursors were also and alternatively cultivated in GM-CSF alone at 1000 IU/ml. The DC were cultivated to day 6, and the culture supernatants from which the dexosomes (DEXm) originated were accumulated from day 3 to day 6. They were then recovered using the procedure described, for example, in French patent applications FR 97 709007 and FR 98 01437, i.e., by differential centrifugation.

The murine and human NK cells were recovered as described in the Method and Apparatus section (point 5).

To show the presence of NK cells and dexosomes, NK cells from the spleens of SCID/BALBc mice were incubated in 96 well conical bottom plates in a concentration of 1.5 million/ml (these splenocytes contained 30% of Dx5+NK). The dexosomes were then added, in an amount of 10–20 μg of exosomal proteins per well (Bradford test), and the cells were recovered at 18–20 hours to carry out the cytoxicity test (against YAC-1 cells) and the gamma interferon production test (supernatant tested in murine IFNg ELISA). The cytotoxicity and interferon measurement tests were carried out as described in the Method and Apparatus section (points 7 and 8).

The results obtained are shown in FIGS. 10 to 13. These results clearly show activation of NK cells by the dexosomes of dendritic cells, with particularly pronounced activation by the dexosomes produced from immature and non triggered dendritic cells. Further, the observed activation crosses the species barrier since human dexosomes activated murine NK cells.

Figure 10A:
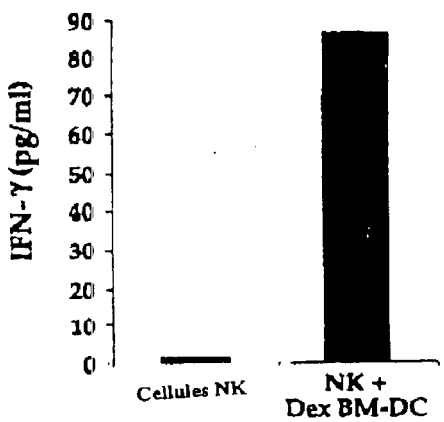
Figure 10B:
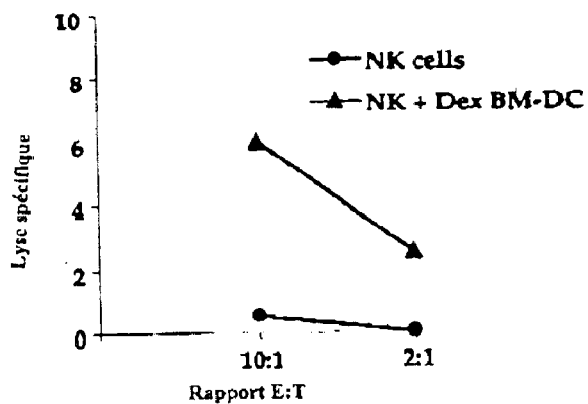
Figure 10C:
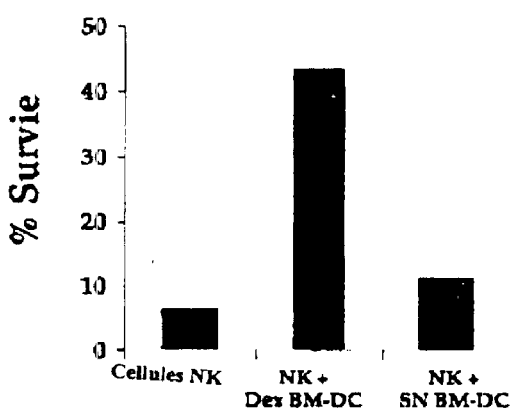
Figure 10D:
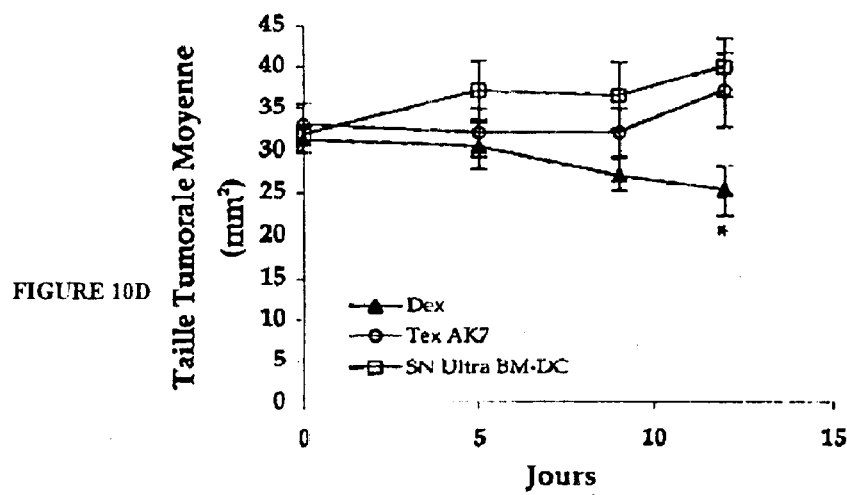

More particularly, FIG. 10(a) shows the production of murine IFNγ by the NK of SCID/BALB/c mice (splenocytes comprising 30% to 40% of Dx5+cells, i.e., NK cells) stimulated by a preparation of exosomes originating from murine dendritic cells cultivated in IL-4+GM-CSF (BM-DC), in a dose of the order of 20 μg/million of Dx5+NK. In this dose, the exosomes also increased the basic cytotoxicity of resting NK (FIG. 10b) and their in vitro survival rate (FIG. 10c), while in the majority of these cases, the direct BM-DC supernatant had no major effect on NK activation (FIG. 10c). The results shown in FIG. 10d also confirm this in vivo activity, since they show a reduction in the average AK7 tumour size in nude mice after administration of dexosomes. These results thus show that exosomes from immature dendritic cells stimulate NK activity. They also show that the activation level is influenced by the dexosome concentration, and that doses of about 10 μg/$10^6$ NK cells or more are preferred for in vitro or ex vivo activation.

The results shown in FIG. 11 also confirm these observations on dexosomes of human dendritic cells. In this experiment, MD-DCs were cultivated in IL-4+GM-CSF for about 9 days. The exosomes (Dexh) secreted by these cells, which were in an essentially immature state, were recovered on day 7 to day 9 or day 6 to day 8. These human dexosomes (Dexh) were incubated under the conditions described above in the presence of murine NK cells, in doses of 20 to 40 μg/million NK cells. The results obtained show stimulation of IFNγ production, demonstrating NK cell activation.

Figure 12A:
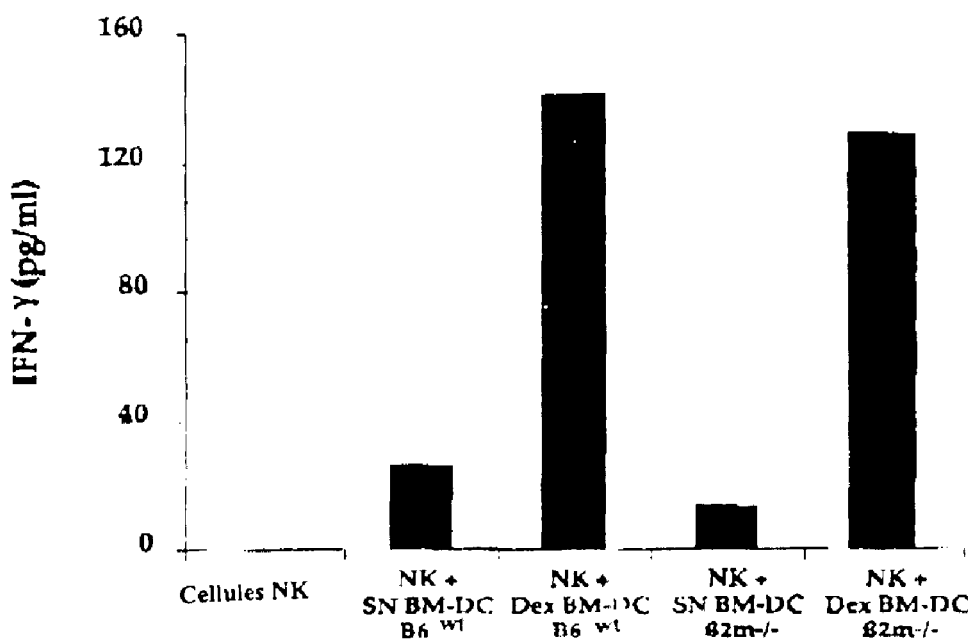
Figure 12B:
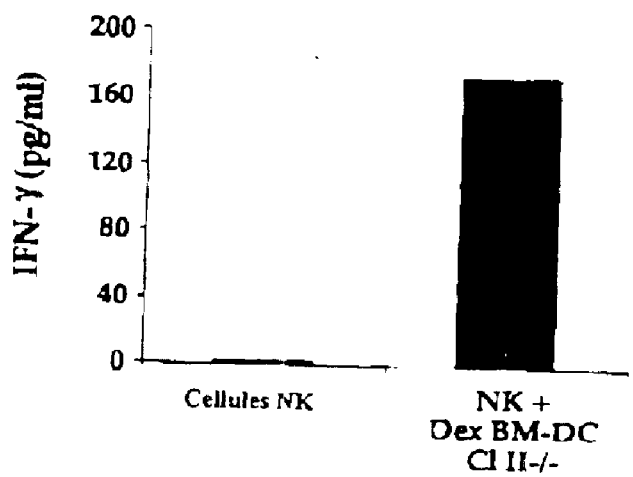

Further, the results shown in FIG. 12 show that the exosomes of murine DC originating from (Knock-Out) mice deficient for the $\beta_2$-microglobulin gene (conventional or related class I MHC molecule) or for class II MHC molecules retained their capacity to stimulate resting NK for the production of IFNγ. These results (i) confirm the stimulating activity of dexosomes and (ii) indicate that the stimulation factor does not appear to be a class I MHC molecule (in contrast to certain elements of the KIRs (killer inhibitory receptor, small) family, or KIRl (killer inhibitory receptor, long) family). The results obtained show that production of IFNγ by NK cells stimulated with DC dexosomes originating from $\beta_2$-microglobulin -/- K.O mice (FIG. 12a) or class II K. O mice (FIG. 12b) is high. NK stimulation has also been observed using entire dendritic cells.

Figure 13A:
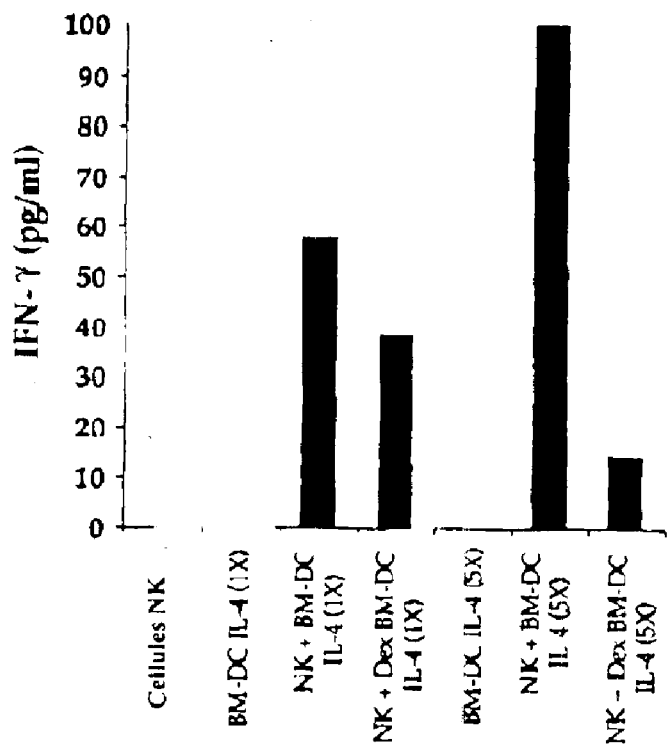

Finally, FIG. 13 shows a certain correlation between the stimulating activity of dendritic cells and the exosomes they secrete. Thus, the results presented show that highly active dendritic cells (for example mature and, if necessary, triggered) secrete less active dexosomes. In contrast, dendritic cells with a lower activity (for example immature dendritic cells or non triggered dendritic cells) secrete very active dexosomes. These elements thus suggest that a transfer, depending on the state of the dendritic cells, of stimulation factor from internal membranous vesicles to the external plasma membrane. More particularly, FIG. 13a shows that DC exosomes cultivated in the presence of GM-CSF and small doses of interleukin-4 (1×) significantly better stimulate NK than their homologues originating from DC cultivated in the presence of GM-CSF and high doses (5×) of IL-4, while the situation is reversed for the DC from which they derive.

Figure 13B:
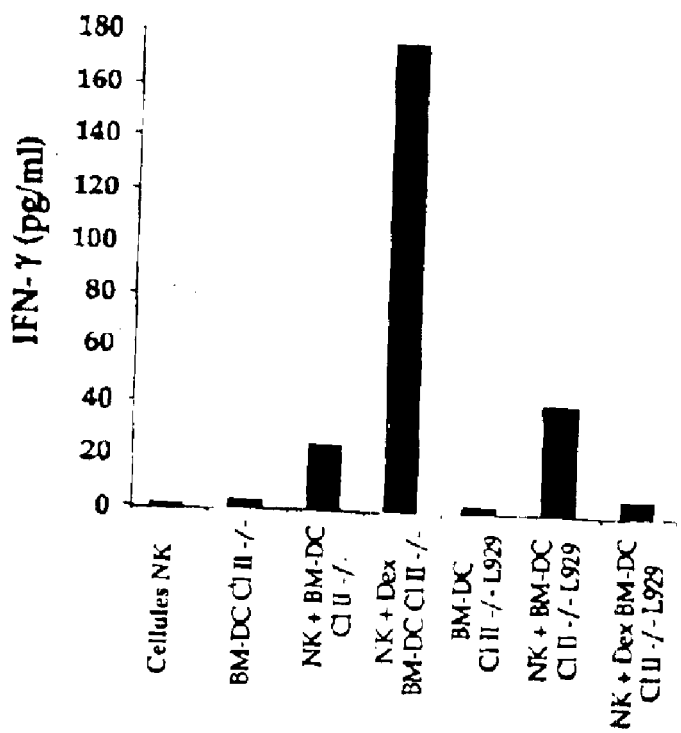

Similarly, FIG. 13b shows that murine exosomes secreted by triggered BM-DC cells (L929 supernatant) stimulate NK cells to a significantly lower extent than their homologues from non triggered BM-DC, and the situation is the reverse for the DC from which they derive. Comparable results were obtained with human dendritic cells.

These results thus show that (i) dexosomes are capable of stimulating resting NK cell activity, (ii) that the most active dexosomes appear to be produced be less active dendritic cells, i.e., immature cells (and possibly non triggered), (iii) that activation by dexosomes crosses the species barrier, (iv) that the stimulation factor responsible for NK activation is on the surface of DEX and presented directly to NK, with or without co-stimulation (other membranous factor or cytokine), and (v) that the stimulation factor does not appear to be a class I MHC molecule. These results thus support the use of dexosomes to activate NK cells in vitro, ex vivo or in vivo.

What is claimed is:

1. A method for producing activated natural killer (NK) cells in vitro or ex vivo, the method comprising bringing an enriched population of resting NK cells into contact with mature or triggered dendritic cells in vitro or ex vivo, under conditions allowing activation of said resting NK cells by said mature or triggered dendritic cells, thereby producing activated NK cells.

2. A method according to claim 1, wherein said dendritic cells are mature human dendritic cells.

3. A method according to claim 1, wherein said dendritic cells are triggered dendritic cells prepared by treating dendritic cells in vitro or ex vivo with a triggering factor or medium selected from a culture of extracellular matrix cells and a supernatant of such cells.

4. A method according to claim 1, wherein said dendritic cells and NK cells are autologous.

5. A method according to claim 1, where said dendritic cells and NK cells are allogenic.

6. A method according to claim 1, wherein the NK cell/dendritic cell ratio is between 0.1 and 10.

7. A method according to claim 1, wherein the NK/dendritic cell ratio is between 0.5 and 5.

8. A method according to claim 2, wherein the NK/dendritic cell ratio is between 0.1 and 10.

9. A method according to claim 2, wherein the NK/dendritic cell ratio is between 0.05 and 5.

10. A method according to claim 3, wherein the NK/dendritic cell ratio is between 0.01 and 10.

11. A method according to claim 3, wherein the NK/dendritic cell ratio is between 0.05 and 5.

12. A method for preparing a drug for the treatment of tumor comprising bringing an enriched population of resting NK cells into contact with mature or triggered dendritic cells in vitro or ex vivo under conditions allowing activation of said resting NK cells by said mature or triggered dendritic cells, thereby producing activated NK cells, and mixing said activated NK cells and a pharmaceutically acceptable vehicle.

13. A method for preparing a drug for the treatment of infected cells comprising bringing an enriched population of resting NK cells into contact with mature or triggered dendritic cells in vitro or ex vivo under conditions allowing activation of said resting NK cells by said mature or triggered dendritic cells, thereby producing activated NK cells, and mixing said activated NK cells and a pharmaceutically acceptable vehicle.

14. A method comprising:
 a) bringing an enriched population of resting human NK cells into contact with mature or triggered dendritic cells in vitro or ex vivo under conditions allowing activation of said human resting NK cells by said mature or triggered dendritic cells, thereby producing activated NK cells;
 b) mixing said activated NK cells of a) with a pharmaceutically acceptable vehicle to produce an injectable composition; and
 c) injecting the injectable composition of b) to a subject, thereby providing activated NK cell activity in said subject.

15. The method of claim 14, wherein said triggered dendritic cells are prepared by treating dendritic cells in vitro or ex vivo with a triggering factor or medium selected from a culture of extracellular matrix cells and a supernatant of such cells.

* * * * *